US010314706B2

(12) United States Patent
Marquez et al.

(10) Patent No.: US 10,314,706 B2
(45) Date of Patent: *Jun. 11, 2019

(54) METHODS OF IMPLANTING A CARDIAC IMPLANT WITH INTEGRATED SUTURE FASTENERS

(71) Applicant: Edwards Lifesciences Corporation, Irvine, CA (US)

(72) Inventors: Salvador Marquez, Foothill Ranch, CA (US); Brian S. Conklin, Orange, CA (US); Manouchehr A. Miraki, Laguna Hills, CA (US); Yoon H. Kwon, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 15/625,801

(22) Filed: Jun. 16, 2017

(65) Prior Publication Data

US 2017/0281346 A1    Oct. 5, 2017

Related U.S. Application Data

(63) Continuation of application No. 15/295,912, filed on Oct. 17, 2016, now Pat. No. 9,968,451, which is a
(Continued)

(51) Int. Cl.
*A61F 2/24* (2006.01)
*A61B 17/04* (2006.01)
*A61B 17/02* (2006.01)

(52) U.S. Cl.
CPC ............ *A61F 2/2445* (2013.01); *A61B 17/02* (2013.01); *A61B 17/0487* (2013.01);
(Continued)

(58) Field of Classification Search
CPC .... A61F 2/2427; A61F 2/2439; A61F 2/2412; A61F 2/2409; A61F 2/2445; A61B 17/0487; A61B 17/0488
See application file for complete search history.

(56) References Cited

U.S. PATENT DOCUMENTS 3,143,742 A    8/1964  Cromie
3,320,972 A    5/1967  High et al.
(Continued)

FOREIGN PATENT DOCUMENTS

EP    0125393 A1    11/1984
EP    0143246 A2    6/1985
(Continued)

OTHER PUBLICATIONS

Krakow, "3F Therapeutics, Inc. Announces the First Clinical Implantation of the 3F Enable Aortic Heart Valve.TM., a Patented, Sutureless Implantation, Replacement Heart Valve Intended to Save Valuable Surgery Time and Reduce Time RelatedComplications . . . " Healthcare Sales & Marketing Network News Feed, Jan. 18, 2005, pp. 1-2.
(Continued)

*Primary Examiner* — Kathleen S Holwerda
*Assistant Examiner* — Christina C Lauer
(74) *Attorney, Agent, or Firm* — Guy Cumberbatch

(57) ABSTRACT

A cardiac implant system including a cardiac implant such as an annuloplasty ring, a prosthetic heart valve, or a valved conduit pre-assembled at the time of manufacture with devices for securing the implant to a heart valve annulus using knotless suture fasteners. The knotless suture fasteners may be embedded within a pliant sealing edge of the cardiac implant, or they may be positioned adjacent to the sealing edge. The knotless suture fasteners are spring-biased so as to grip onto annulus anchoring sutures pass to therethrough
(Continued)

upon removal of a restraining device, such as a hypotube inserted within the suture fasteners. Guide tubes are assembled in line with the suture fasteners to permit introduction of suture snares that pass through the suture fasteners and through the sealing edge to facilitate capture of the pre-installed annulus anchoring sutures.

20 Claims, 15 Drawing Sheets

Related U.S. Application Data continuation of application No. 14/302,733, filed on Jun. 12, 2014, now Pat. No. 9,468,527.

(60) Provisional application No. 61/834,356, filed on Jun. 12, 2013.

(52) U.S. Cl.
CPC .......... *A61F 2/2409* (2013.01); *A61F 2/2412* (2013.01); *A61F 2/2448* (2013.01); *A61B 2017/0237* (2013.01); *A61B 2017/0488* (2013.01)

(56) References Cited

U.S. PATENT DOCUMENTS

| | | |
|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,340,091 A | 7/1982 | Skelton et al. |
| 4,343,048 A | 8/1982 | Ross |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A * | 2/1988 | Lane .................. A61F 2/2412 623/2.18 |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,690,654 A * | 11/1997 | Ovil .................. A61F 2/2427 606/148 |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |

(56) References Cited

U.S. PATENT DOCUMENTS

| | | | |
|---|---|---|---|
| 6,066,160 A * | 5/2000 | Colvin | A61B 17/0487 606/151 |
| 6,074,418 A | 6/2000 | Buchanan et al. | |
| 6,081,737 A | 6/2000 | Shah | |
| 6,083,179 A | 7/2000 | Oredsson | |
| 6,099,475 A | 8/2000 | Seward et al. | |
| 6,106,550 A | 8/2000 | Magovern et al. | |
| 6,110,200 A | 8/2000 | Hinnenkamp | |
| 6,117,091 A | 9/2000 | Young et al. | |
| 6,126,007 A | 10/2000 | Kari et al. | |
| 6,264,611 B1 | 7/2001 | Ishikawa et al. | |
| 6,322,526 B1 | 11/2001 | Rosenman et al. | |
| 6,350,282 B1 | 2/2002 | Eberhardt | |
| 6,475,230 B1 * | 11/2002 | Bonutti | A61B 17/0487 606/232 |
| 6,491,624 B1 | 12/2002 | Lotfi | |
| 6,773,457 B2 | 8/2004 | Ivancev et al. | |
| 7,037,333 B2 | 5/2006 | Myers et al. | |
| 7,235,086 B2 | 6/2007 | Sauer et al. | |
| 7,862,584 B2 | 1/2011 | Lyons et al. | |
| 7,998,151 B2 | 8/2011 | St. Goar et al. | |
| 8,308,798 B2 | 11/2012 | Pintor et al. | |
| 8,323,337 B2 | 12/2012 | Gurskis et al. | |
| 8,348,998 B2 | 1/2013 | Pintor et al. | |
| 9,017,347 B2 * | 4/2015 | Oba | A61B 17/0487 606/144 |
| 9,468,527 B2 | 10/2016 | Marquez et al. | |
| 2001/0021872 A1 | 9/2001 | Bailey et al. | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0049492 A1 | 12/2001 | Frazier et al. | |
| 2002/0026238 A1 | 2/2002 | Lane et al. | |
| 2002/0032481 A1 | 3/2002 | Gabbay | |
| 2002/0058995 A1 | 5/2002 | Stevens | |
| 2002/0123802 A1 | 9/2002 | Snyders | |
| 2002/0138138 A1 | 9/2002 | Yang | |
| 2002/0151970 A1 | 10/2002 | Garrison et al. | |
| 2002/0188348 A1 | 12/2002 | DiMatteo et al. | |
| 2002/0198594 A1 | 12/2002 | Schreck | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0036795 A1 | 2/2003 | Andersen et al. | |
| 2003/0040792 A1 | 2/2003 | Gabbay | |
| 2003/0055495 A1 | 3/2003 | Pease et al. | |
| 2003/0105519 A1 | 6/2003 | Fasol et al. | |
| 2003/0109924 A1 | 6/2003 | Cribier | |
| 2003/0114913 A1 | 6/2003 | Spenser et al. | |
| 2003/0130729 A1 | 7/2003 | Paniagua et al. | |
| 2003/0149478 A1 | 8/2003 | Figulla et al. | |
| 2003/0167089 A1 | 9/2003 | Lane | |
| 2003/0236568 A1 | 12/2003 | Hojeibane et al. | |
| 2004/0019374 A1 | 1/2004 | Hojeibane et al. | |
| 2004/0034411 A1 | 2/2004 | Quijano et al. | |
| 2004/0044406 A1 | 3/2004 | Woolfson et al. | |
| 2004/0106976 A1 | 6/2004 | Bailey et al. | |
| 2004/0122514 A1 | 6/2004 | Fogarty et al. | |
| 2004/0122516 A1 | 6/2004 | Fogarty et al. | |
| 2004/0167573 A1 | 8/2004 | Williamson et al. | |
| 2004/0186563 A1 | 9/2004 | Lobbi | |
| 2004/0186565 A1 | 9/2004 | Schreck | |
| 2004/0193261 A1 | 9/2004 | Berreklouw | |
| 2004/0206363 A1 | 10/2004 | McCarthy et al. | |
| 2004/0210304 A1 | 10/2004 | Seguin et al. | |
| 2004/0210305 A1 | 10/2004 | Shu et al. | |
| 2004/0210307 A1 | 10/2004 | Khairkhahan | |
| 2004/0225355 A1 | 11/2004 | Stevens | |
| 2004/0236411 A1 | 11/2004 | Sarac et al. | |
| 2004/0260389 A1 | 12/2004 | Case et al. | |
| 2004/0260390 A1 | 12/2004 | Sarac et al. | |
| 2005/0010285 A1 | 1/2005 | Lambrecht et al. | |
| 2005/0027348 A1 | 2/2005 | Case et al. | |
| 2005/0033398 A1 | 2/2005 | Seguin | |
| 2005/0043760 A1 | 2/2005 | Fogarty et al. | |
| 2005/0043790 A1 | 2/2005 | Seguin | |
| 2005/0060029 A1 | 3/2005 | Le et al. | |
| 2005/0065594 A1 | 3/2005 | DiMatteo et al. | |
| 2005/0065614 A1 | 3/2005 | Stinson | |
| 2005/0075584 A1 | 4/2005 | Cali | |
| 2005/0075713 A1 | 4/2005 | Biancucci et al. | |
| 2005/0075717 A1 | 4/2005 | Nguyen et al. | |
| 2005/0075718 A1 | 4/2005 | Nguyen et al. | |
| 2005/0075719 A1 | 4/2005 | Bergheim | |
| 2005/0075720 A1 | 4/2005 | Nguyen et al. | |
| 2005/0075724 A1 | 4/2005 | Svanidze et al. | |
| 2005/0080454 A1 | 4/2005 | Drews et al. | |
| 2005/0096738 A1 | 5/2005 | Cali et al. | |
| 2005/0137682 A1 | 6/2005 | Justino | |
| 2005/0137686 A1 | 6/2005 | Salahieh et al. | |
| 2005/0137687 A1 | 6/2005 | Salahieh et al. | |
| 2005/0137688 A1 | 6/2005 | Salahieh et al. | |
| 2005/0137689 A1 | 6/2005 | Salahieh et al. | |
| 2005/0137690 A1 | 6/2005 | Salahieh et al. | |
| 2005/0137691 A1 | 6/2005 | Salahieh et al. | |
| 2005/0137692 A1 | 6/2005 | Haug et al. | |
| 2005/0137694 A1 | 6/2005 | Haug et al. | |
| 2005/0137695 A1 | 6/2005 | Salahieh et al. | |
| 2005/0137702 A1 | 6/2005 | Haug et al. | |
| 2005/0159811 A1 | 7/2005 | Lane | |
| 2005/0165477 A1 | 7/2005 | Anduiza et al. | |
| 2005/0165479 A1 | 7/2005 | Drews et al. | |
| 2005/0182483 A1 | 8/2005 | Osborne et al. | |
| 2005/0182486 A1 | 8/2005 | Gabbay | |
| 2005/0192665 A1 | 9/2005 | Spenser et al. | |
| 2005/0203616 A1 | 9/2005 | Cribier | |
| 2005/0203617 A1 | 9/2005 | Forster et al. | |
| 2005/0203618 A1 | 9/2005 | Sharkawy et al. | |
| 2005/0216079 A1 | 9/2005 | MaCoviak | |
| 2005/0222674 A1 | 10/2005 | Paine | |
| 2005/0234546 A1 | 10/2005 | Nugent et al. | |
| 2005/0240259 A1 | 10/2005 | Sisken et al. | |
| 2005/0251252 A1 | 11/2005 | Stobie | |
| 2005/0261765 A1 | 11/2005 | Liddicoat | |
| 2005/0283231 A1 | 12/2005 | Haug et al. | |
| 2006/0004410 A1 | 1/2006 | Nobis et al. | |
| 2006/0025857 A1 | 2/2006 | Bergheim et al. | |
| 2006/0052867 A1 | 3/2006 | Revuelta et al. | |
| 2006/0058871 A1 | 3/2006 | Zakay et al. | |
| 2006/0058872 A1 | 3/2006 | Salahieh et al. | |
| 2006/0074484 A1 | 4/2006 | Huber | |
| 2006/0085060 A1 | 4/2006 | Campbell | |
| 2006/0095125 A1 | 5/2006 | Chinn et al. | |
| 2006/0122634 A1 | 6/2006 | Ino et al. | |
| 2006/0122692 A1 | 6/2006 | Gilad et al. | |
| 2006/0136054 A1 | 6/2006 | Berg et al. | |
| 2006/0149360 A1 | 7/2006 | Schwammenthal et al. | |
| 2006/0154230 A1 | 7/2006 | Cunanan et al. | |
| 2006/0161249 A1 | 7/2006 | Realyvasquez et al. | |
| 2006/0167543 A1 | 7/2006 | Bailey et al. | |
| 2006/0195183 A1 | 8/2006 | Navia et al. | |
| 2006/0195184 A1 | 8/2006 | Lane et al. | |
| 2006/0195185 A1 | 8/2006 | Lane et al. | |
| 2006/0195186 A1 | 8/2006 | Drews et al. | |
| 2006/0207031 A1 | 9/2006 | Cunanan et al. | |
| 2006/0229708 A1 | 10/2006 | Powell et al. | |
| 2006/0235508 A1 | 10/2006 | Lane et al. | |
| 2006/0241745 A1 | 10/2006 | Solem | |
| 2006/0246888 A1 | 11/2006 | Bender et al. | |
| 2006/0253191 A1 | 11/2006 | Salahieh et al. | |
| 2006/0259134 A1 | 11/2006 | Schwammenthal et al. | |
| 2006/0259135 A1 | 11/2006 | Navia et al. | |
| 2006/0259136 A1 | 11/2006 | Nguyen et al. | |
| 2006/0265010 A1 | 11/2006 | Paraschac et al. | |
| 2006/0265056 A1 | 11/2006 | Nguyen et al. | |
| 2006/0271172 A1 | 11/2006 | Tehrani | |
| 2006/0271175 A1 | 11/2006 | Woolfson et al. | |
| 2006/0287717 A1 | 12/2006 | Rowe et al. | |
| 2006/0287719 A1 | 12/2006 | Rowe et al. | |
| 2006/0293745 A1 | 12/2006 | Carpentier et al. | |
| 2007/0005129 A1 | 1/2007 | Damm et al. | |
| 2007/0010876 A1 | 1/2007 | Salahieh et al. | |
| 2007/0010877 A1 | 1/2007 | Salahieh et al. | |

(56) References Cited

U.S. PATENT DOCUMENTS

| | | |
|---|---|---|
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270907 A1 | 11/2007 | Stokes et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0021546 A1 | 1/2008 | Patz et al. |
| 2008/0033543 A1 | 2/2008 | Gurskis et al. |
| 2008/0065198 A1 | 3/2008 | Quintessenza |
| 2008/0119875 A1 | 5/2008 | Ino et al. |
| 2008/0154356 A1 | 6/2008 | Obermiller et al. |
| 2008/0234729 A1 | 9/2008 | Page et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0161036 A1 | 6/2010 | Pintor et al. |
| 2010/0249894 A1 | 9/2010 | Oba et al. |
| 2010/0249908 A1 | 9/2010 | Chau et al. |
| 2010/0331972 A1 | 12/2010 | Pintor et al. |
| 2011/0022165 A1 | 1/2011 | Oba et al. |
| 2011/0147251 A1 | 6/2011 | Hodshon et al. |
| 2012/0065729 A1 | 3/2012 | Pintor et al. |
| 2012/0150288 A1 | 6/2012 | Hodshon et al. |
| 2013/0053949 A1 | 2/2013 | Pintor et al. |
| 2013/0116777 A1 | 5/2013 | Pintor et al. |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

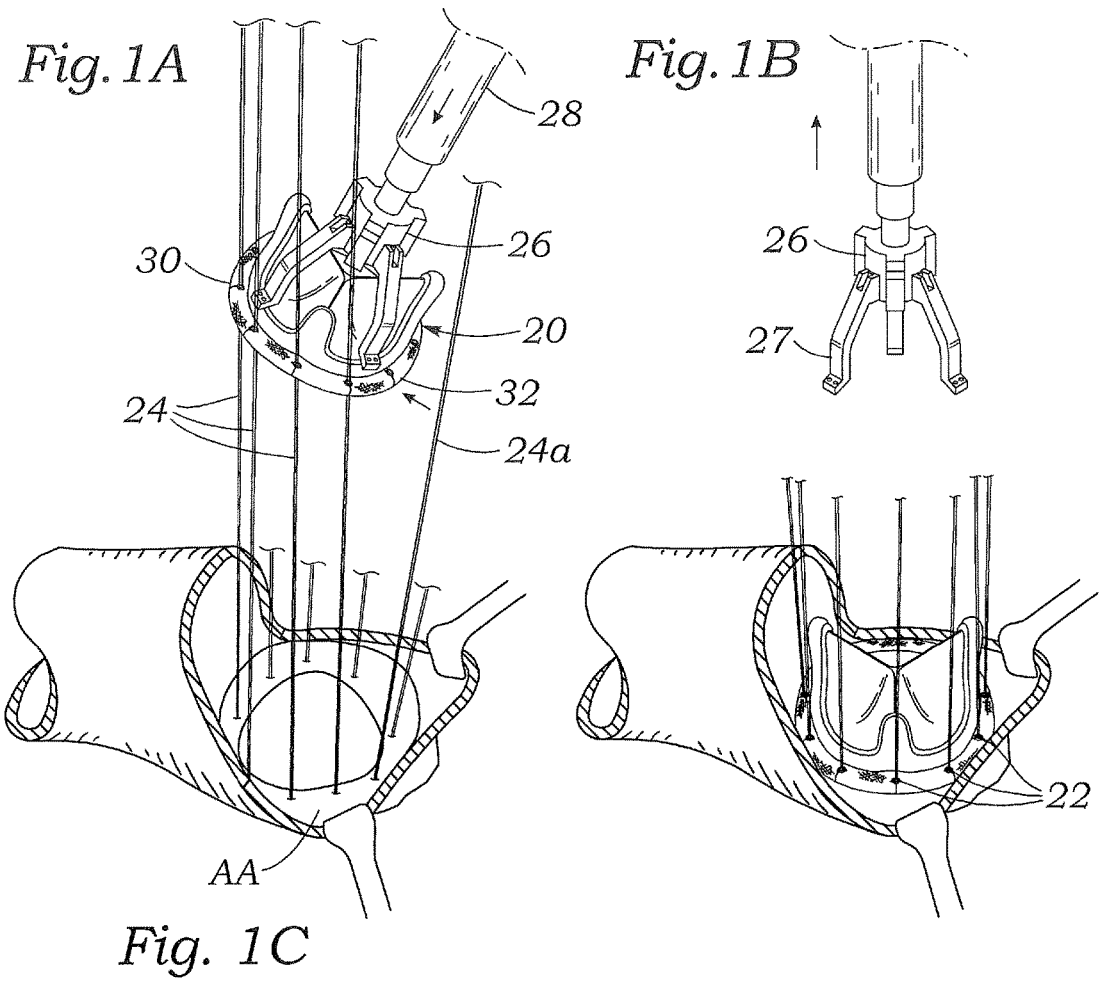
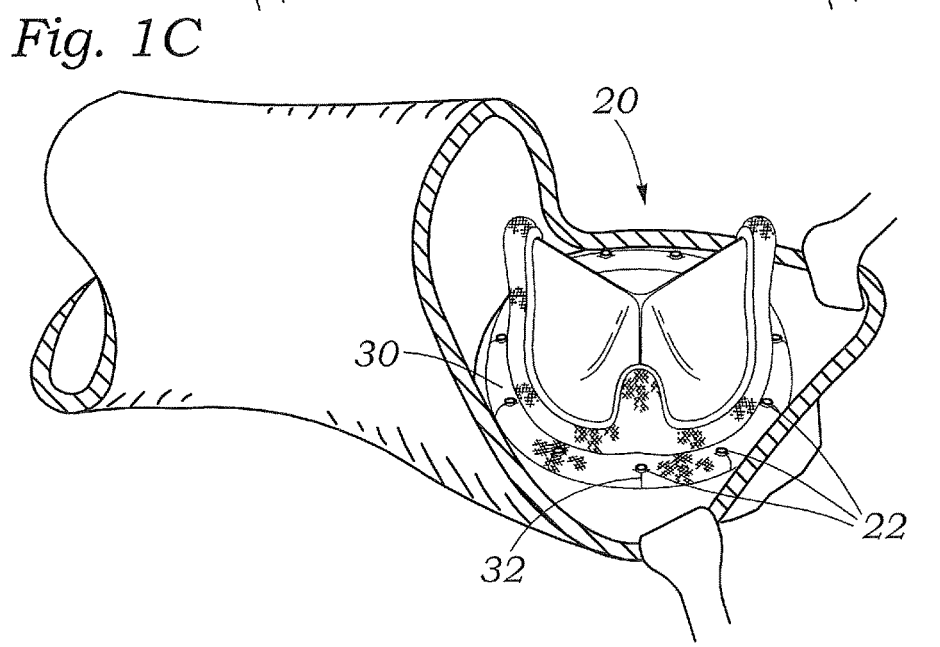

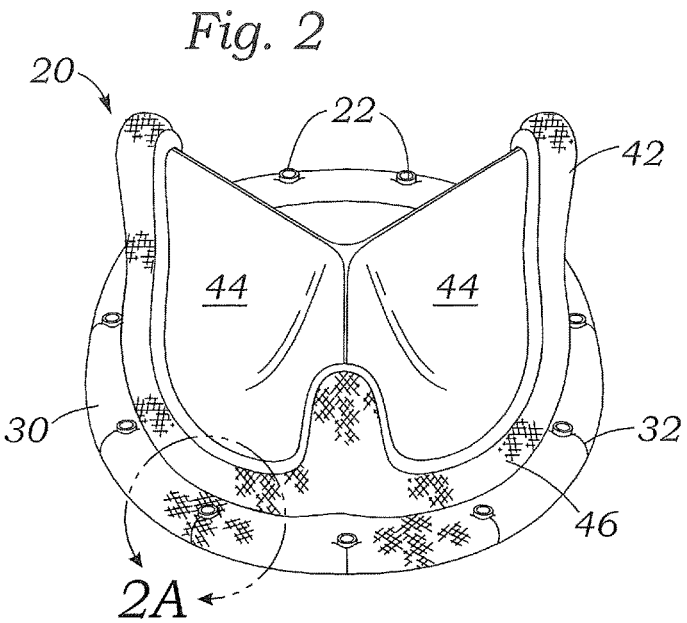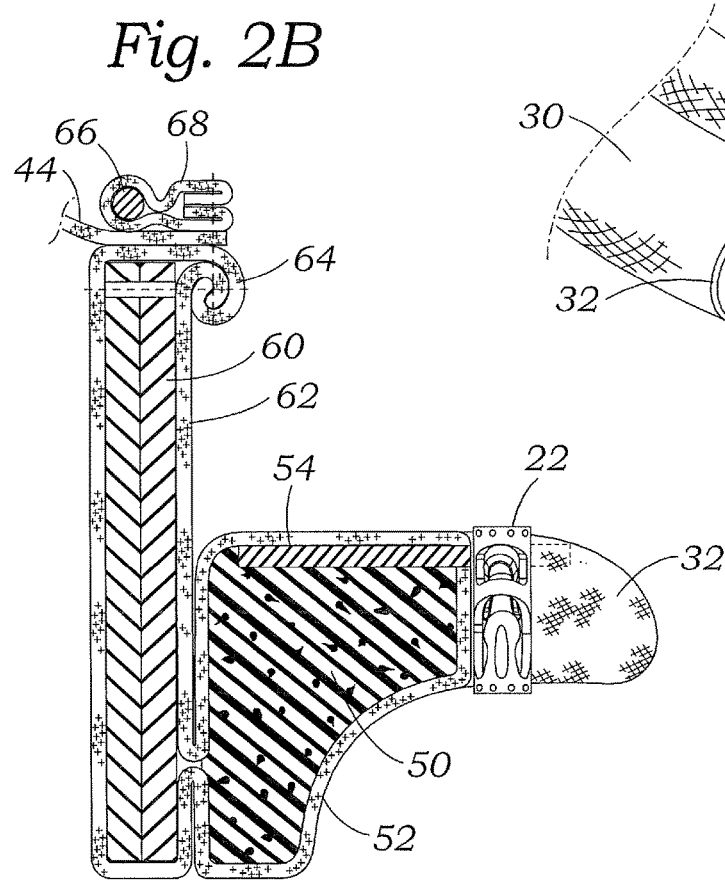

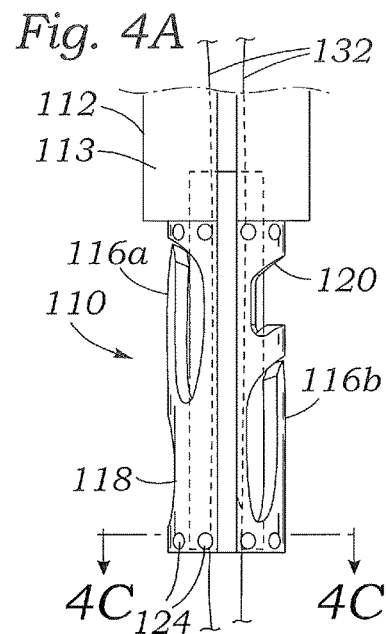
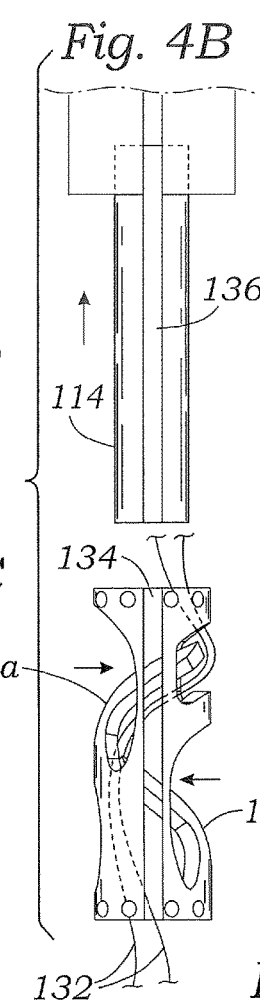
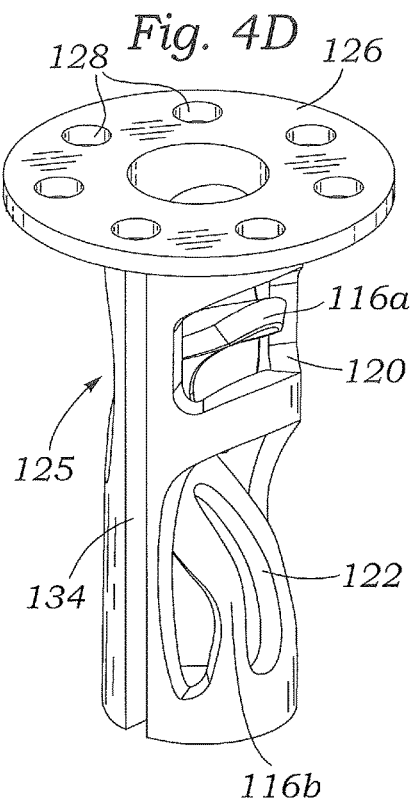
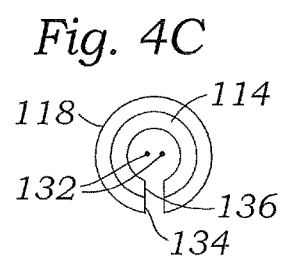
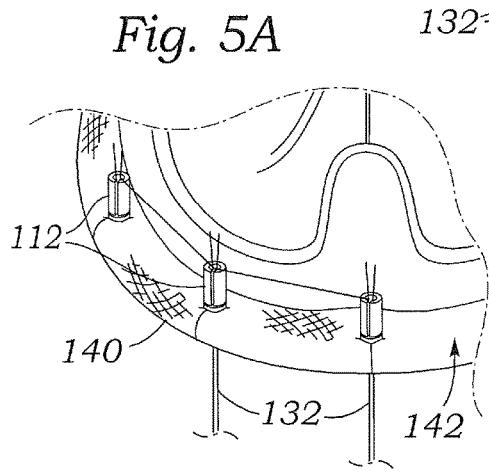
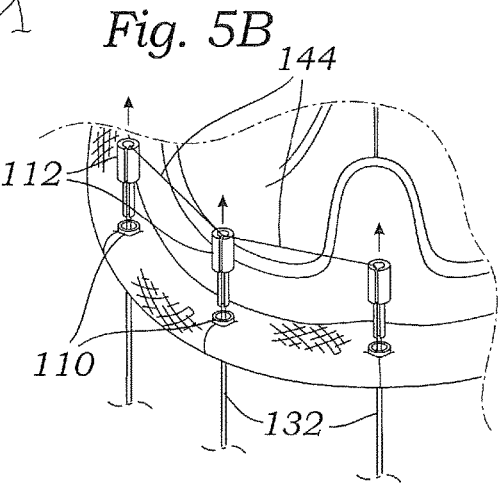

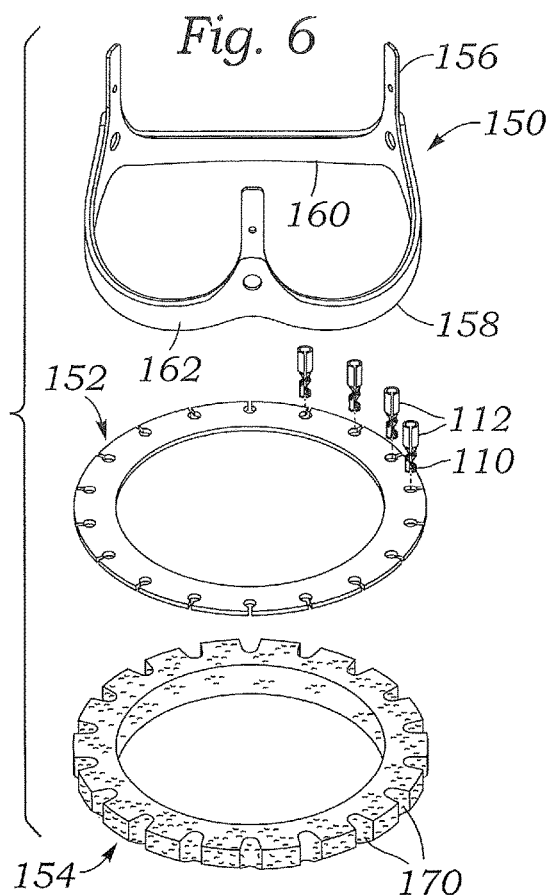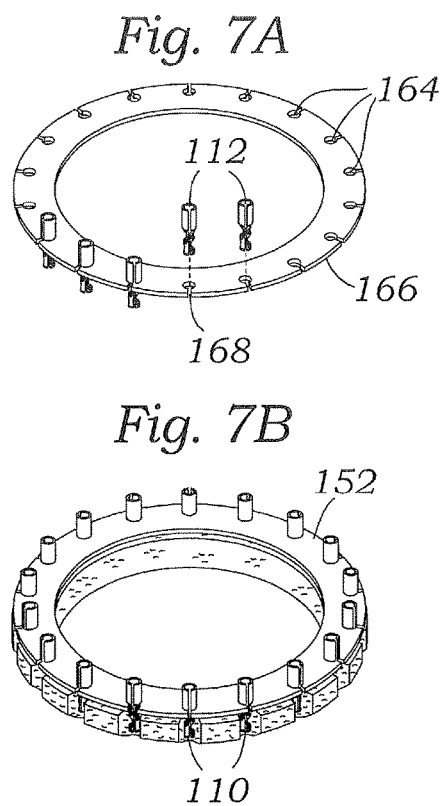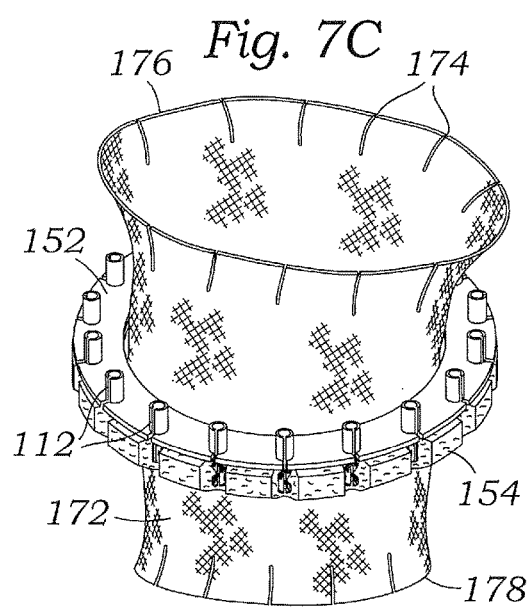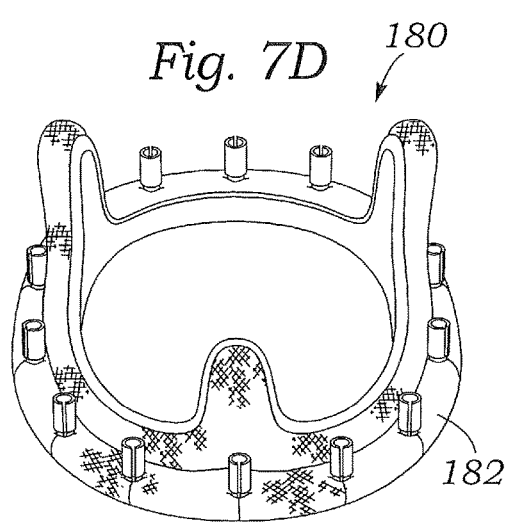

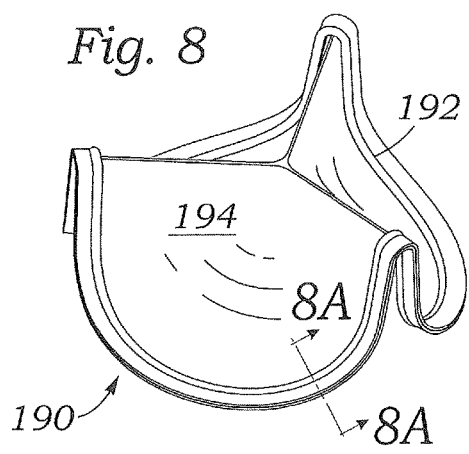
Fig. 8
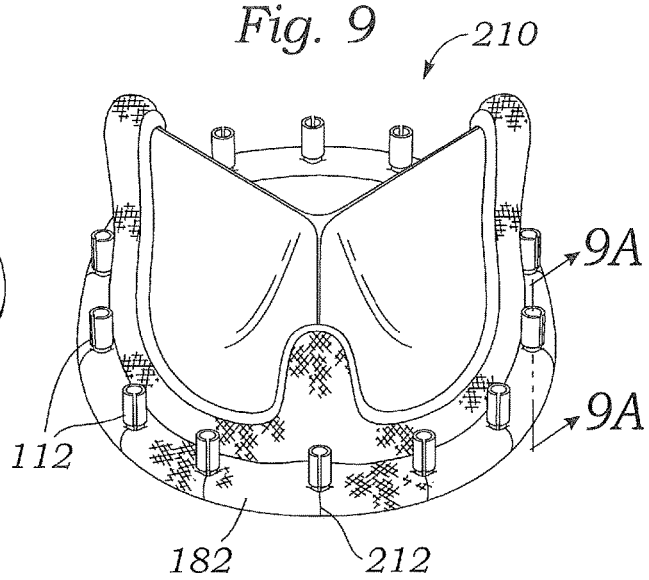
Fig. 9
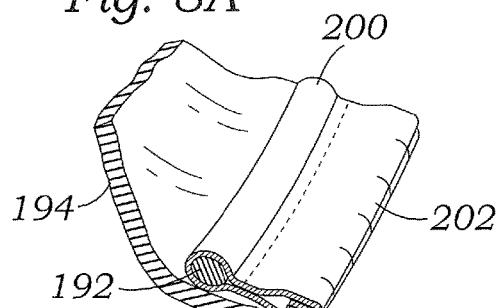
Fig. 8A
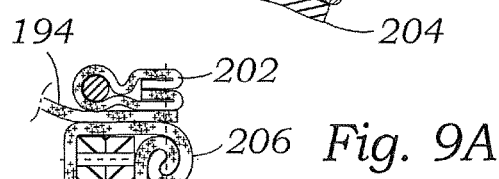
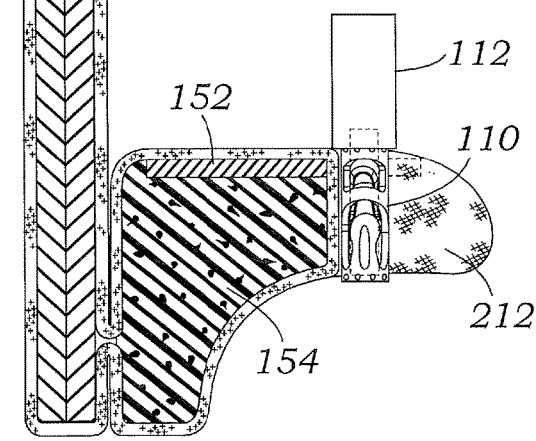
Fig. 9A
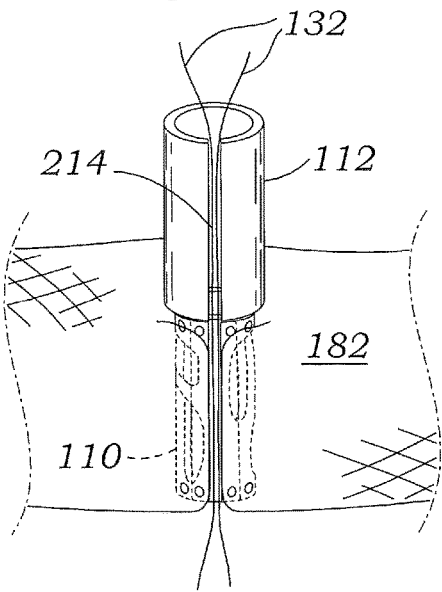
Fig. 9B

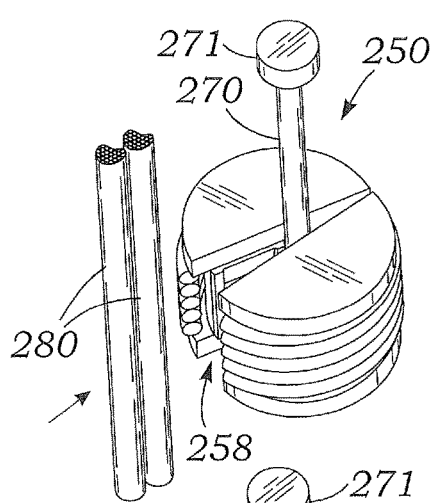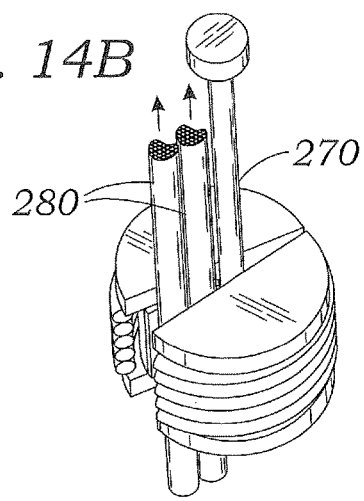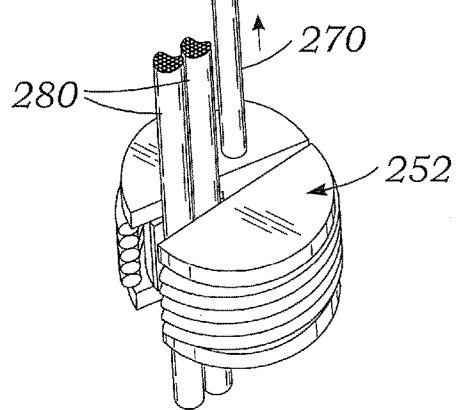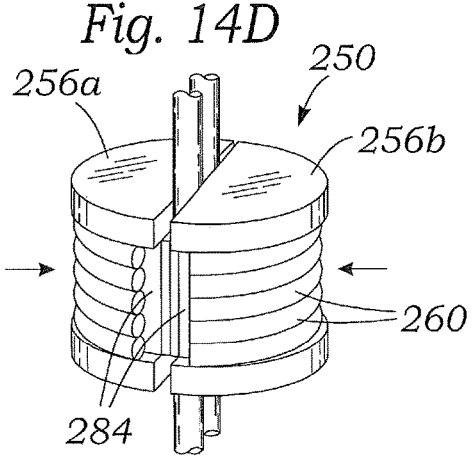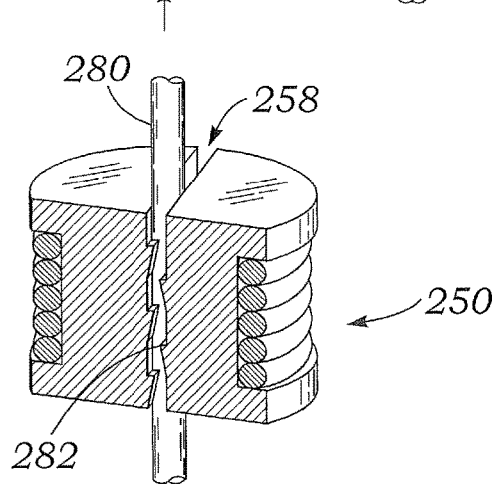

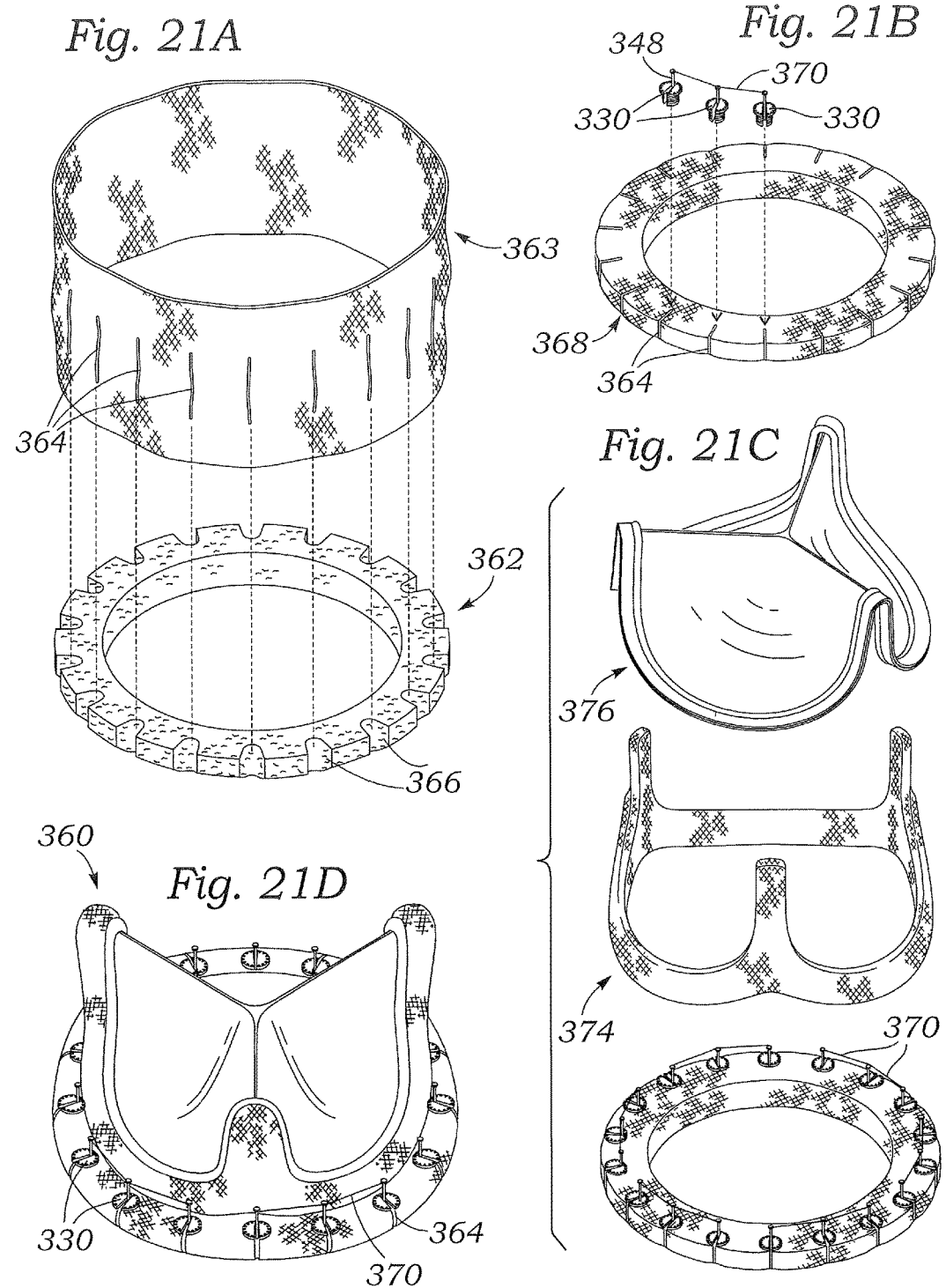

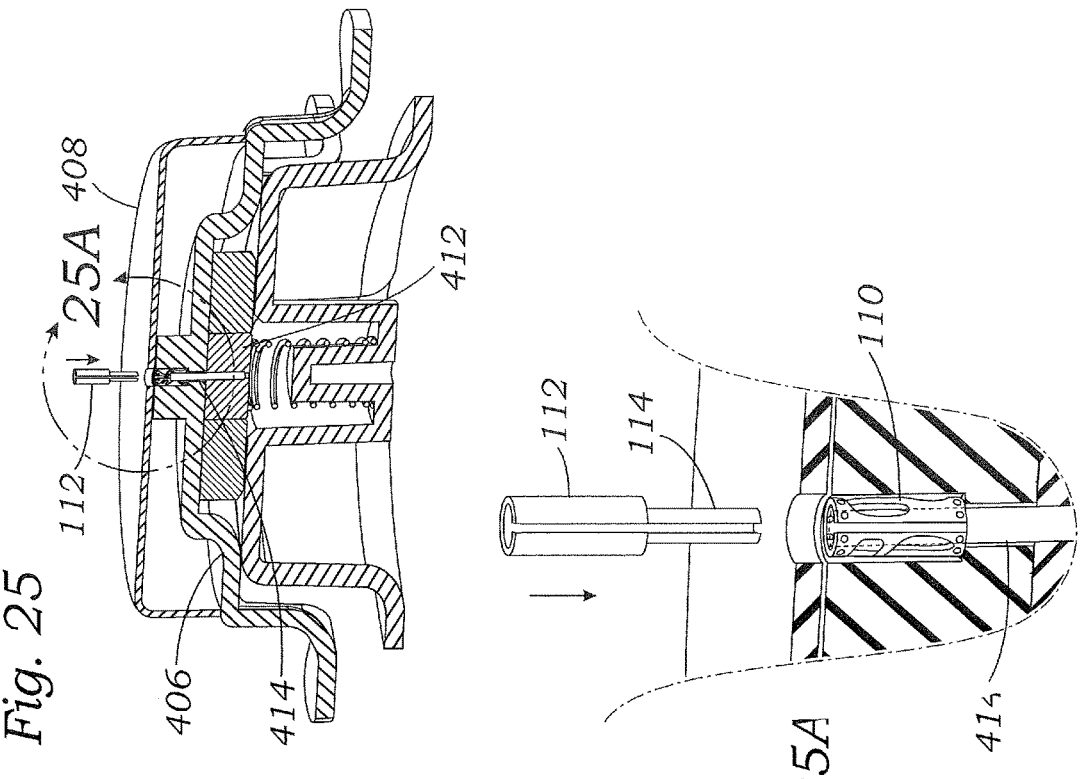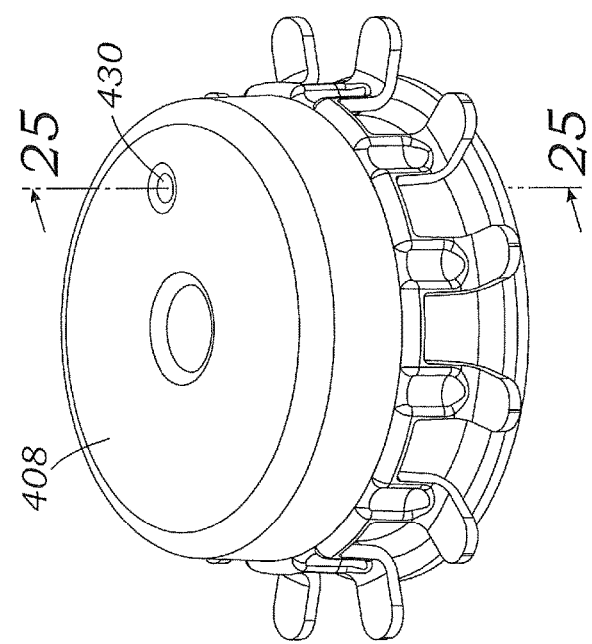

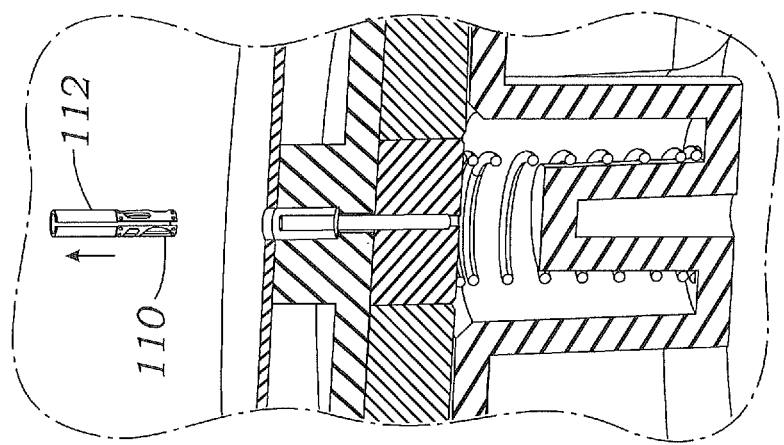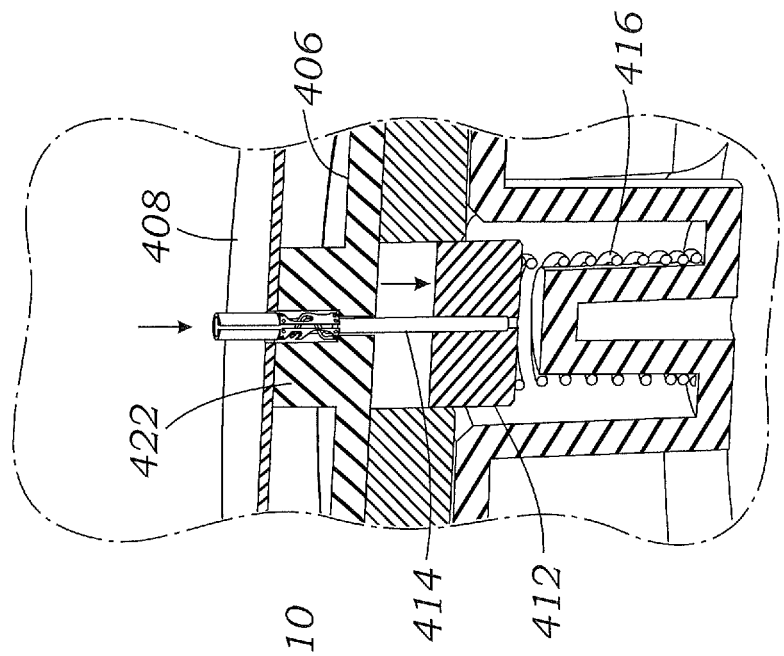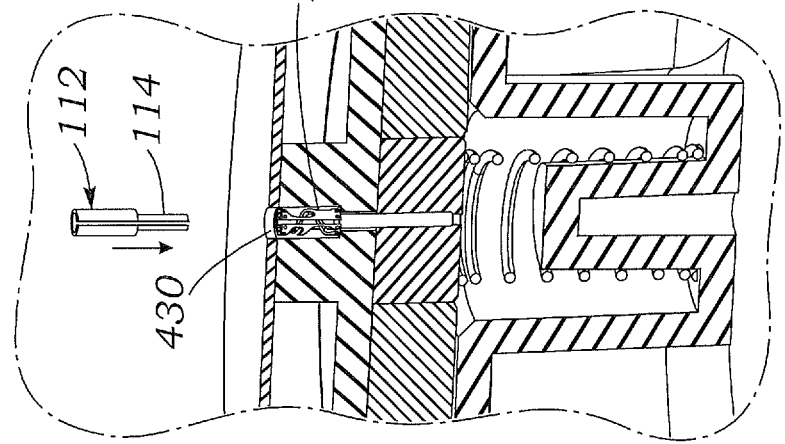

METHODS OF IMPLANTING A CARDIAC IMPLANT WITH INTEGRATED SUTURE FASTENERS

RELATED APPLICATIONS

This application is a continuation of U.S. patent application Ser. No. 15/295,912, filed Oct. 17, 2016, which is a continuation of U.S. patent application Ser. No. 14/302,733, filed Jun. 12, 2014, now U.S. Pat. No. 9,468,527, which claims the benefit of U.S. Patent Application No. 61/834,356, filed Jun. 12, 2013, the entire disclosures all of which are incorporated by reference.

FIELD OF THE INVENTION

The present invention relates generally to a prosthetic cardiac implant having a knotless suture fastening system assembled therewith for securing the valve to a native annulus without requiring suture knots.

BACKGROUND OF THE INVENTION

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood or regurgitation through the valve when the leaflets are supposed to coapt together. Valve disease can be severely debilitating and even fatal if left untreated.

Various surgical techniques may be used to repair a diseased or damaged valve, including securing a cardiac implant to the diseased annulus. Cardiac implants include prosthetic heart valves, valved conduits and annuloplasty rings. In a valve replacement operation, the damaged leaflets are excised and the annulus sculpted to receive a replacement valve. Worldwide, approximately 300,000 heart valve replacement surgeries are performed annually, and about one-half of these patients received mechanical heart valves, which are composed of rigid, synthetic materials. The remaining patients received bioprosthetic heart valve replacements, which utilize biologically derived tissues for flexible fluid occluding leaflets. Prosthetic heart valves may be implanted independently in one of the orifices or annuluses of the heart, or may be coupled to a flow conduit which extends in line with the valve a predetermined distance. For example, valved conduits can be designed for reconstruction of portions of the flow passage above and below the aortic valve, such as the ascending aorta, in addition to replacing the function of the valve itself. Another less drastic method for treating defective valves is through repair or reconstruction, which is typically used on minimally calcified valves. One repair technique that has been shown to be effective in treating incompetence is annuloplasty, in which the deformed valve annulus is reshaped by attaching a prosthetic annuloplasty repair segment or ring to the valve annulus.

In a typical cardiac implant procedure, the aorta is incised and, in a valve replacement operation, the defective valve is removed leaving the desired placement site that may include a fibrous tissue layer or annular tissue. Known cardiac implant techniques include individually passing sutures through the fibrous tissue or desired placement site within the valve annulus to form an array of sutures. Free ends of the sutures are extended out of the thoracic cavity and are spaced apart, sometimes being distributed around a suture organizer. The free ends of the sutures are then individually threaded through a suture-permeable sealing edge of the annuloplasty ring or prosthetic heart valve. Once all sutures have been run through the sealing edge (typically 12 to 18 sutures), all the sutures are pulled up taught and the prosthesis is slid or "parachuted" down until it sits against the target annulus. The cardiac implant is then secured in place by traditional knot tying of the anchoring sutures on the proximal side of the sealing edge. This procedure is time consuming as doctors often use three to ten knots per suture.

During open-heart procedures, the patient is on heart-lung bypass which reduces the patient's oxygen level and creates non-physiologic blood flow dynamics. The longer a patient is on heart-lung bypass, the greater the risk for complications including permanent health damage. Existing techniques for suturing cardiac implants extend the duration of bypass and increase the health risks due to heart-lung bypass. Furthermore, the securing force created by suturing varies significantly because the pre-tensioning of the suture just prior to knot tying is difficult to consistently maintain, even for the same medical professional.

There exists a need for devices and methods that reduce the time required to secure a heart valve repair prosthesis in place. Currently a clinician must tie a multitude of knots in sutures which can take a great deal of time and lengthens the time a patient is on cardio-pulmonary bypass and under anesthesia. Additionally, there exists a need to make it easier to secure a heart valve repair prosthesis (e.g., an annuloplasty ring) in place. Currently, a clinician must work in the limited space near the heart to tie knots in sutures. This is a cumbersome process that benefits from a clinician of great dexterity and patience.

SUMMARY OF THE INVENTION

The present invention provides improved knotless suture fasteners and systems for securing a cardiac implant such as an annuloplasty ring or a prosthetic heart valve or valved conduit to a heart valve annulus. The apparatus and methods are particularly well suited for traditional surgery or minimally invasive surgery. The devices disclosed herein eliminate the need for surgical knots thus reducing surgical time and exposure. Further, the devices improve the ease of implantation because the clinician need not tie knots in the limited space in and around the heart. The knotless suture fasteners are simple to deploy and their actuation does not affect suture tension. The implant systems are pre-assembled at the time of manufacture with the cardiac implants. The knotless suture fasteners may be embedded within a pliant sealing edge of the cardiac implant, or they may be positioned on one face of the sealing edge. One embodiment of the knotless suture fasteners includes small tubes having tabs that are spring-biased inward so as to grip onto annulus anchoring sutures passing therethrough upon removal of a restraining device, such as a hypotube inserted within the tubular suture fasteners. Another embodiment includes a bifurcated locking clamp, a biasing member positioned on the outside of the locking clamp, and a retention member positioned between the clamp halves. Regardless of what type of fastener is used, it is positioned adjacent a slit in the sealing edge such that the physician need not pass needles through the sealing edge to engage the implant sutures with the fastener.

A preferred cardiac implant system comprises a cardiac implant having an inner frame arranged around a flow axis through the implant along which blood will flow when implanted from an inflow side to an outflow side of the implant. A pliant sealing edge extends outward from the inner frame and has inflow and outflow faces. The sealing edge also has formed therein a plurality of generally axial slits that open radially outward. A plurality of knotless suture fasteners are distributed around the sealing edge and attached thereto. Each fastener has an axial slot sized to receive a suture facing radially outward, and each fastener is located adjacent one of the axial slits in the sealing edge such that a suture may be passed through the slit and into the axial slot of the fastener. The fasteners have an open state which permits a suture to slide axially therethrough and a closed state which prevents axial movement of the suture in at least one direction. The fasteners may be at least partially embedded into and secured in the sealing edge, or may be positioned on one of the inflow or outflow faces of the sealing edge and attached thereto.

In the aforementioned cardiac implant system, each suture fastener may have an outer wall defining a lumen extending from a proximal end to a distal end and a collapsible wall structure, wherein the collapsible wall structure in the open state does not restrict relative movement between the fastener and a suture therein and the collapsible wall structure in the closed state restricts movement of a suture through the fastener in at least one direction. In this configuration, each fastener further includes a retention member coupled thereto in the open state, the retention member having a hypotube which fits closely within the lumen of the fastener and maintains the collapsible wall structure in its open state, and upon removal of the retention member and hypotube, the fastener converts to the closed state and the collapsible wall structure collapses inward to clamp onto a suture. In an embodiment where the suture fastener is embedded in the sealing edge, a flange extends outward from the outer wall at a proximal end thereof sufficiently large to prevent the fastener from pulling through the pliant sealing ring.

In an alternative embodiment, each suture fastener comprises a bifurcated locking clamp including a pair of substantially similar clamp halves each having an exterior surface and an inner surface facing the inner surface of the other clamp half to form a variable sized slot therebetween. The clamp halves are connected for movement toward or away from one another while being fixed axially with respect to one another, wherein the suture(s) extend through the slot between the inner surfaces of the clamp halves. A biasing member positioned on the outside of the locking clamp has a relaxed size that, in the absence of an object in the slot, urges the inner surfaces of the clamp halves together. Finally, a retention member is positioned between the clamp halves against the force of the biasing member and has a thickness that maintains the slot width large enough to permit passage of a suture therethrough, wherein removal of the retention member permits the biasing member to urge the inner surfaces of the clamp halves together and clamp the suture therebetween. The clamp halves may be molded from a single piece of material with a living hinge on the first circumferential side. The clamp halves are desirably hinged together on a first circumferential side such that the variable sized slot defines a variable sized opening on the side opposite the first circumferential side, and wherein the biasing member comprises a plurality of C-clips arranged around the locking clamp with their free ends located on either side of the variable sized slot opposite the first circumferential side.

For the fasteners disclosed herein, a retention member coupled to the fastener maintains the fastener in the open state and when removed converts the fastener to the closed state, and wherein a plurality of the retention members may be tethered together.

The cardiac implant may be a prosthetic heart valve comprising occluding members that provide one-way flow through the valve movably mounted to move within the inner frame, wherein the pliant sealing edge comprises a sealing ring secured to the outside of the inner frame. There may be only three of the suture fasteners located around the sealing ring. Further, the inner frame may partly extend in an outflow direction to form three cantilevered commissures evenly distributed around the flow axis that support flexible leaflets, and the prosthetic heart valve further includes a plastically-expandable anchoring skirt coupled to the sealing ring and extending from an inflow end thereof, the three suture fasteners being located around the sealing ring intermediate the commissures. Alternatively, the cardiac implant is an annuloplasty ring, wherein the inner frame comprises a structural core and the pliant sealing edge surrounds the core and has a fabric cover. In yet another embodiment, the cardiac implant is a valved conduit, comprising a valve having a conduit coupled thereto and having a sealing edge surrounding the inflow end.

An exemplary method of securing a cardiac implant to a heart valve annulus, comprises:

providing a pre-assembled cardiac implant system including an implant having an inner frame surrounding a flow axis through the implant along which blood will flow when implanted from an inflow side to an outflow side of the implant, the implant including a pliant sealing edge extending outward from the inner frame with a plurality of generally axial slits that open radially outward, the system further including a plurality of knotless suture fasteners attached to and distributed around the sealing edge at the locations of the axial slits;

pre-installing at least one anchoring suture at the heart valve annulus, each anchoring suture being passed at least once through the heart valve annulus with free end(s) extending away from the annulus;

passing each of the free end(s) of the anchoring sutures radially inward through one of the axial slits in the sealing edge and into the corresponding suture fastener;

advancing the cardiac implant until the pliant sealing edge seats against the annulus;

deploying the suture fasteners to clamp onto the free end(s) of the anchoring sutures; and severing each of the free end(s) of the anchoring sutures close to the proximal end of the respective suture fastener.

The cardiac implant may be a prosthetic heart valve, and the inner frame partly extends in an outflow direction to form three cantilevered commissures evenly distributed around the flow axis. The valve also has three flexible leaflets each supported by two of the commissures with a free edge therebetween that coapts with the other flexible leaflet free edges along the flow axis to provide one-way flow through the valve. The pliant sealing edge therefore comprises a sealing ring secured to the outside of the inner frame. The prosthetic heart valve may further include an anchoring skirt coupled to the sealing ring and extending from an inflow end thereof, and the method includes expanding the anchoring skirt below the heart valve annulus, wherein the method of securing the prosthetic heart valve to the annulus consisting only of expanding the anchoring skirt and attaching the three sutures and suture fasteners.

In one aspect of the method described above, each of the suture fasteners is embedded within the sealing edge of the cardiac implant. The implant may alternatively be an annuloplasty ring, wherein the inner frame may comprise a metallic core and the pliant sealing edge comprises a silicone sleeve surrounding the core and a fabric cover over the sleeve. Each fastener preferably includes a retention member such as a retention pin that when coupled to the fastener maintains the fastener in the open state and when removed converts the fastener to the closed state, wherein a plurality of the retention pins are tethered together and the method includes sequentially removing a plurality of retention pins that are tethered together from adjacent fasteners.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIGS. 1A-1C are drawings of several steps in a procedure for implanting a heart valve at an aortic annulus using the techniques and an exemplary "side entry" knotless fastener of the present application;

FIG. 2 is a perspective view of a flexible leaflet prosthetic heart valve after deployment of a plurality of exemplary tubular side entry fasteners distributed around a peripheral sealing edge;

FIG. 2A is an enlarged view of one tubular knotless suture fastener in the prosthetic heart valve of FIG. 2, while FIG. 2B is a cross-section therethrough showing the fastener embedded in a pliant sealing ring;

FIG. 3A is an enlarged view of a tubular side entry fastener in the annuloplasty ring of FIG. 3, while

FIGS. 4A-4C are enlarged and sectional views showing a tubular side entry fastener and retention pin isolated from the cardiac implants for clarity, while FIG. 4D shows an alternative configuration of the tubular fastener;

FIGS. 5A and 5B show the tubular side entry fastener embedded in a sealing ring of a prosthetic heart valve before and after deployment;

FIG. 6 is a perspective view of several internal components a flexible leaflet prosthetic heart valve and a plurality of the tubular side entry fasteners;

FIG. 7A is a perspective view of a disk-shaped sealing ring insert having holes around its periphery for receiving the tubular side entry fasteners and retention pins;

FIG. 7B is a perspective view of the sealing ring insert of FIG. 7A above a sealing ring sponge and having the tubular fasteners extending within outer recesses formed within the sponge;

FIG. 7C is a perspective view of the components in FIG. 7B with a tubular fabric piece disposed within the annular sponge prior to wrapping and sewing around the sub assembly;

FIG. 7D is a perspective view of a stent subassembly of the components shown exploded in FIG. 6 covered and joined together with fabric;

FIG. 8 is a perspective view of a leaflet subassembly of a fabric-covered undulating wireform having flexible leaflets attached thereto and extending inward into a flow orifice defined thereby, and FIG. 8A is a sectional view through one edge of the leaflet subassembly;

FIG. 9 is a perspective view of a completed prosthetic heart valve having the tubular side entry fasteners and corresponding retention pins around its sealing ring periphery, and illustrating small vertical slits in the outer edge of the sealing ring at the circumferential location of the fasteners;

FIG. 9A is a sectional view through the prosthetic heart valve of FIG. 9 showing the position of one of the tubular side entry fasteners within the sealing ring;

FIG. 9B is an enlarged view of one of the side entry fasteners looking directly radially inward through the vertical slit in the sealing ring of FIG. 9;

FIG. 11 shows just the bifurcated locking clamp, while

FIGS. 14A-14D are perspective views of a sequence of operation of the side entry suture fastener;

FIG. 15 is a perspective sectional view of the side entry suture fastener clamped onto a suture that is pre-attached at one end to the device, and showing how the suture(s) can be tensioned further;

FIG. 17A is an enlarged view of one of the side entry fasteners looking directly radially inward through the vertical slit in the sealing ring of FIG. 16A and prior to deployment, while

FIGS. 21A-21D illustrate several components and steps in assembling a prosthetic heart valve having the embedded side entry fasteners of FIGS. 19-20;

FIG. 23 is a perspective assembled view of the loading fixture of FIG. 22, while

FIG. 24 is a perspective view of the loading fixture;

FIGS. 25 and 25A are sectional views through the load station in which the retention pin is entering showing a retention pin entering the lead-in cavity; and FIGS. 26A-26C are sectional views through one of the load stations showing steps in transferring an exemplary suture fastener from the load station to the retention pin.

DETAILED DESCRIPTION OF THE PREFERRED EMBODIMENTS

Figure 3:
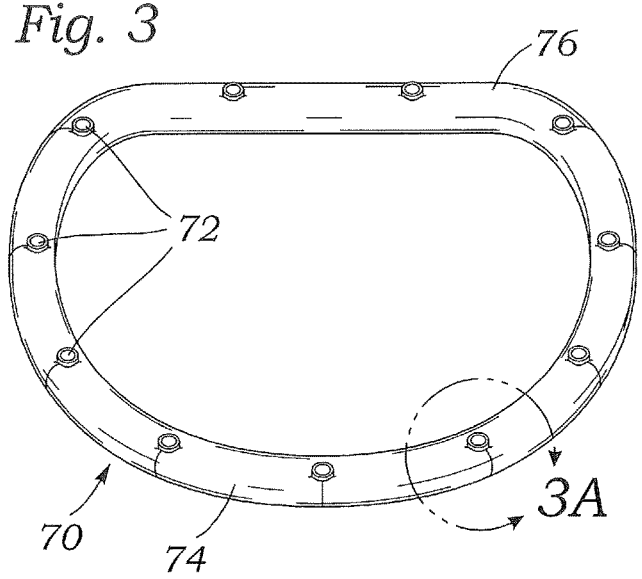
FIG. 3 is a plan view of an exemplary annuloplasty ring having embedded tubular side entry fasteners.

The present invention provides improved systems for securing a cardiac implant to a heart valve annulus using knotless fasteners. The systems described herein each includes a prosthetic implant pre-assembled with the knotless fasteners. The term "pre-assembled" means that the cardiac implants are assembled by the manufacture and packaged along with the suture fasteners which are positioned for deployment. In one version, the suture fasteners are embedded within a sealing edge on the cardiac implant, while in another version the suture fasteners are positioned in contact with a proximal face of the sealing edge. Proximal and distal refer to the opposite directions toward and away, respectively, from a surgeon performing the implant. In either case, because the suture fasteners are pre-assembled with the cardiac implant and positioned for deployment, their installation is greatly facilitated.

The knotless suture fasteners described herein include self-actuating or spring-loaded devices that clamp onto sutures. Passing one or more sutures through the device and then converting it from an open to a closed state causes features to collapse inward and clamp onto the suture(s). The conversion desirably occurs upon removal of an impediment to inward motion of clamping elements, though other spring-loaded configurations are possible. Such self-actuating suture fasteners are preferred over plastically-deformable fasteners which must be crimped over the sutures using forceps or other such compression tools. On the other hand, for added security a portion of the suture fasteners disclosed herein may be deformable so that a user may crimp it onto the sutures—a hybrid fastener. For the purpose of defining terms, the term "self-actuating" suture fastener refers to a spring-biased type of device which does not require crimping, but which, on the other hand, does not exclude a crimpable portion. A "self-actuating" suture fastener is not entirely autonomous, in that there is a trigger prior to the deployment, such as removal of an element or change in temperature, but the term excludes devices that require mechanical crimping using an external tool.

Alternative self-actuating fasteners may be made of a temperature-activated memory material that biases the fastener to its closed configuration when exposed to a selected temperature range, though the control and timing of such devices add complexity. With the temperature-activated memory material in its austenite state, the fastener tabs extend into the inner lumen to their greatest extent, so that the fastener is in a "closed" configuration wherein the tabs block movement of any lengths of suture passing through the inner lumen. The austenite state can be set to occur when the suture fastener is generally unstressed and at human body temperature, so that when deployed in the patient's body it will be remain biased toward its closed configuration.

It should also be understood that a suture fastener that is not at all spring-loaded, but instead is entirely plastically deformable may be used. For example, a rivet-style suture fastener may be positioned adjacent to or embedded within a cardiac implant sealing edge, as with the exemplary self-actuating suture fastener. Although not shown, tools for crimping or actuating such alternative suture fasteners may be included in the implant system. In short, though there are distinct advantages to a self-actuating or spring-loaded fastener, certain aspects of the present application may be exploited while using a fastener that is crimped onto the anchoring sutures, and the disclosure should not be considered limited to one type of fastener or another unless explicit in any one claim.

The term cardiac implant as used herein primarily refers to prosthetic heart valves, valved conduits and annuloplasty rings or segments. However, the suture fastening systems described herein can be used to attach other prostheses such as stents, grafts, stent-grafts, fluid delivery reservoirs, electro-stimulators, or the like. Furthermore, the cardiac implants are desirably secured at a target heart valve annulus, but the suture fastening systems may also be used to attach implants to other anatomical structures such as vessels, organs (e.g., intestine, heart, skin, liver, kidney) or other locations where sutures are typically used to attach the implant.

FIGS. 1A-1C illustrate several steps in a surgical procedure for implanting a prosthetic heart valve 20 at an aortic annulus AA, which is exposed by forming an incision in the ascending aorta or aortic arch. The heart valve 20 is representative of numerous types of heart valves, including those with flexible leaflets as shown, and also mechanical valves with rigid metallic leaflets. Further, the flexible leaflet heart valve 20 is shown with a plurality of "side-entry" suture fasteners 22 of the present application deployed from an outflow side of the valve, which typically indicates that the valve is for implant at the aortic annulus where the outflow is also the proximal side relative to conventional heart valve delivery. However, it should be understood that the suture fasteners 22 could be reversed within the heart valve 20 so that they are deployed from the inflow side, such as in a mitral valve replacement procedure. Therefore, the present implant system is suitable for aortic valves, mitral valves and even pulmonic valves which are less common.

The implant procedure illustrated is typical of surgical heart valve replacement procedures, where the surgeon initially loops a plurality of individual sutures 24 through the aortic annulus AA so as to form an array of pairs of sutures extending upward out of the operating site. In a conventional surgical procedure, each separate pair of sutures 24 is then passed through a pliant sewing ring of the heart valve. By positioning pairs of sutures 24 around the sewing ring at circumferential locations corresponding to where they pass through the aortic annulus AA, the surgeon can then "parachute" the heart valve down the array of sutures until the sewing ring seats against the aortic annulus AA. Subsequently, the pairs of sutures are tied off on the proximal side of the sewing ring to secure the valve to the annulus. The sewing ring is pliant and conforms to the often uneven annulus, thereby greatly reducing paravalvular leakage. Sewing rings are typically formed of rolled fabric or silicone rubber sponges surrounded by fabric.

In contrast, the present application contemplates a number of configurations of exemplary "side entry" knotless fasteners which both eliminate the necessity to pass a needle through a sewing ring and also eliminate the process of tying the sutures off with knots. This both reduces the possibility of damaging the heart valve with a suture needle, and greatly reduces the time necessary to secure the valve to the annulus.

FIG. 1A shows the heart valve 20 secured on a holder 26 that in turn is coupled to the distal end of a delivery handle

28. A plurality of pairs of sutures 24 have already been inserted into knotless fasteners 22 distributed around a sealing ring 30 of the valve, while one pair 24*a* is shown just prior to engagement with a knotless fastener within the sealing ring. As seen, the suture pair 24*a* is displaced radially toward a slit 32 in the outer edge of the sealing ring 30, which leads to a knotless fastener within the sealing ring, as will be described below. Although the heart valve 20 is shown just above the aortic annulus AA, this procedure may be done outside of the patient's body entirely. It should also be noted pairs of free ends of a looped suture are typically used when knots are tied, but since the fasteners 22 are "knotless," a single stranded suture may be passed through the aortic annulus AA with a pledget at the end anchored under the annulus. In either case, a suture is anchored to the annulus by either looping it or anchoring with a pledget with free end(s) extending upward out of the implant site for coupling with the fasteners 22. From here on the term "a suture" refers to one or a pair of sutures.

Each fastener 22 has an open state which permits a suture 24 to slide axially therethrough and a closed or deployed state which prevents axial movement of the suture 24 in at least one direction. In a preferred embodiment, each of the knotless fasteners 22 may be deployed so as to retain the sutures 24 therein, while still permitting the surgeon to slide the heart valve 20 down the array of sutures. The process of engaging each suture 24 with one of the knotless fasteners 22 continues until all of the suture pairs are positioned around the heart valve sealing ring 30, after which time the valve is parachuted down the array of sutures until the sealing ring seats against the aortic annulus AA. The sealing ring 30 may be configured like the sewing rings of conventional valves, such as with rolled fabric or fabric-covered silicone, but no sutures are passed through it and thus it is not called a sewing ring. The sealing ring 30 provides a sealing edge at its outmost extent.

FIG. 1B shows the heart valve 20 seated at the aortic annulus AA and after disconnection of the valve holder 26. In the illustrated embodiment, the holder 26 has 3 legs 27 that connect to valve cusps via sutures which can be severed to disengage the holder from the valve 20. The holder 26 and delivery handle 28 are typically removed from the implantation site prior to severing the free ends of sutures 24, and otherwise checking for proper implantation. Finally, FIG. 1C shows the heart valve 20 after implantation with all of the sutures cut at the level of the sealing ring 30. The implantation site can then be closed up.

FIG. 2 is a perspective view of the prosthetic heart valve 20 after deployment of a plurality of exemplary tubular side entry fasteners 22 distributed around the peripheral sealing ring 30, while FIG. 2A is an enlarged view of the fastener and FIG. 2B is a cross-section showing the fastener embedded in the sealing ring. The flexible leaflet heart valve 20 preferably includes an internal frame or stent (FIG. 2B) which has a cloth cover and defines three upstanding commissure posts 42 that support three flexible leaflets 44 therebetween. The sealing ring 30 attaches around the periphery of the internal frame at the inflow end of the valve, with the commissure posts 42 projecting in the outflow direction. The leaflets 44 can be formed from separate flaps of xenograft tissue, such as bovine pericardium, or all three leaflets can be derived from a single xenograft valve, such as a porcine valve. The leaflets 44 are secured and supported by the commissure posts 42, as well as along arcuate cusps 46 in between the commissure posts.

There are desirably between 12-20 knotless suture fasteners 22 distributed around the sealing ring 30. The number of suture fasteners 22 partly depends on the size of the valve 20, with more fasteners being used on larger valves. Furthermore, suture fasteners 22 may be placed at strategic locations, such as adjacent to the commissure posts 42. Preferably, there is one suture fastener 22 aligned with each of the commissure posts 42, and a number of suture fasteners evenly distributed between the commissure posts along the cusps 46. For instance, three suture fasteners 22 may be distributed between the commissure posts 42 such that one of them is centered in each of the cusps 46, for a total of twelve suture fasteners.

FIG. 2A shows one of the tubular suture fasteners 22 embedded in the sealing ring 30. An upper edge of the fastener 22 projects above the sealing ring 30, while the majority of the body of the fastener is within the sealing ring. The axis of the tubular fastener 22 generally corresponds to the central axis of the heart valve, which is synonymous with vertical. The fastener 22 includes a vertical opening 48 in one side thereof which is oriented radially outward toward and in line with the vertical slit 32 formed in the sealing ring 30. The combination of the aligned slit 32 and opening 48 provides the entryway for the sutures 24 to pass into the inner lumen of the tubular fastener 22.

Now with reference to FIG. 2B, certain inner components of the prosthetic heart valve 20 are illustrated, which can also be seen in greater detail in FIGS. 6-9. The fastener 22 illustrated is located in one of the cusps 46 of the valve 20, and a section through one of the commissures 42 would be somewhat different. The sealing ring 30 comprises an inner sponge member 50 having a fabric cover 52. In a preferred embodiment, an annular planar retention disc 54 is assembled with the sealing ring 30. As will be explained below, the retention disc 54 is positioned on top of the sponge member 50 and has a plurality of apertures for holding the fasteners 22. It should be understood that the retention disc 54 could also have an undulating shape to match the upper surface of non-planar sealing rings, such as the sewing ring shape of valve models 3000-3300 and 7300 made by Edwards Lifesciences of Irvine, Calif.

An inner wall of the sealing ring 30 attaches to a stent member 60 also having a fabric covering 62. At the top of the stent member 60, the fabric covering is rolled into a sewing tab 64. An outer edge of one of the valve leaflets 44 is sandwiched between the top edge of the stent member 60 including the sewing tab 64 and a wireform 66 having a fabric covering 68. Sutures hold the components together.

Figure 3A:
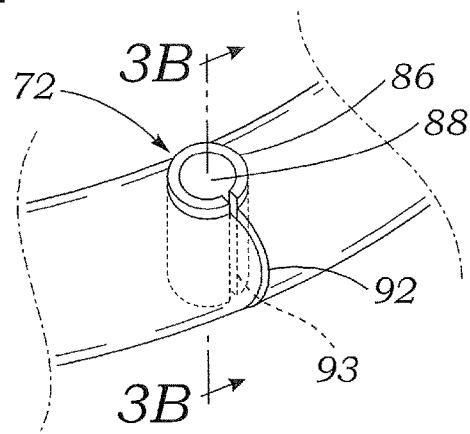
Figure 3B:
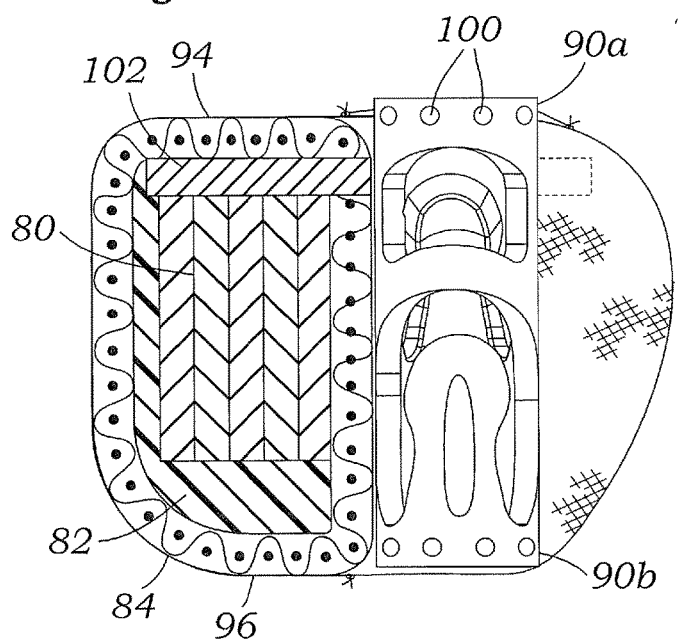
FIG. 3B is a cross-section therethrough showing the fastener embedded in a sealing edge.

FIG. 3 is a plan view of an exemplary annuloplasty ring 70 having tubular side entry fasteners 72 embedded in a pliant sealing edge, while FIG. 3A is an enlarged view of a fastener and FIG. 3B is a cross-section therethrough. Annuloplasty rings can be continuous or open, rigid, semi-rigid, or more flexible, and the present application contemplates all types. The annuloplasty ring 70 illustrated in FIG. 3 is configured for implant at a mitral annulus, and as such has a plan view as seen which is generally oval and slightly D-shaped with a more pronounced curve along the lower or posterior segment 74 as opposed to the upper or anterior segment 76. The outer ends of the relatively straight anterior segment 76 approximately corresponds to the expected location of fibrous trigones around the mitral valve annulus on either side of the anterior leaflet. In illustrated embodiment, there are eleven knotless suture fasteners 72 distributed around the periphery of the annuloplasty ring 70. Desirably, fasteners 72 are located adjacent the trigones, and one is located adjacent the midpoint of the posterior segment 74, with the rest being distributed evenly therebetween.

FIG. 3A illustrates the suture fastener 72 embedded within a pliant sealing edge of the annuloplasty ring 70. The annuloplasty ring 70 comprises an inner core 80, typically metallic, surrounded by a silicone sleeve 82 which, in turn, is enclosed within a fabric cover 84. The illustrated inner core 80 comprises a plurality of concentric bands, though other rigid and semi-rigid structures such as a solid titanium ring are often utilized. A pliant sealing edge may comprise a portion of the silicone sleeve 82 and fabric cover 84 which project outward from the inner core 80. It should be understood that the materials of the pliant sealing edge may be other than silicone and fabric, such as all fabric for example. If the ring is entirely flexible, such as being made entirely of a silicone band surrounded by a fabric cover, then the entire ring can be considered the sealing edge and the suture fasteners can be positioned anywhere through the ring. The sealing edge may be configured like the pliant outer edges of conventional annuloplasty rings, such as with rolled fabric or fabric-covered silicone, but no sutures are passed through it and thus it is not called a sewing edge.

Each fastener 72 has an open state which permits a suture to slide axially therethrough, and a closed or deployed state which prevents axial movement of the suture in at least one direction. More particularly, the exemplary knotless suture fastener 72 has a generally tubular outer wall 86 defining a lumen 88 having a diameter extending from a proximal end 90a to a distal end 90b. The outer wall 86 is interrupted by a collapsible wall structure for contacting and holding a suture length within the lumen 88. The suture enters the fastener 72 through a vertical slit 92 in the outer periphery of the annuloplasty ring 70 and a vertical opening 93 in the fastener. As will be further described below, the collapsible wall structure has an open state that does not restrict relative movement between the fastener 72 and a suture therein and is biased toward a closed or deployed state that restricts distal movement of a suture through the fastener without preventing proximal movement.

As seen in FIG. 3B, the proximal end 90 of the suture fastener 72 projects slightly above a proximal face 94 of the annuloplasty ring 70. The distal end 92 desirably lies flush with or slightly above the distal face 96, as shown, though it may project slightly below the distal face 96. The distance that the fastener 72 can project from either face depend somewhat on the particular valve annulus at which the cardiac implant is secured, but typically neither end of the fastener extends more than 3 mm above or below the implant.

FIG. 3B shows an exemplary configuration for securing the suture fastener 72 within the annuloplasty ring 70. In particular, a plurality of attachment threads 98 loop through small holes 100 at the proximal and distal ends 34, 36 and tie off through the fabric cover 84. The tubular suture fastener 72 may first be pushed through the soft sealing edge using a leading punch or awl-type of device (not shown). Other configurations for securing the suture fastener 72 in the illustrated position within the annuloplasty ring 70 are contemplated. For example, flanges on either end may be provided which retained the fastener in position, one of the flanges being spring-loaded so that it may first be retracted for insertion into the soft annuloplasty ring. Alternatively, the fastener may be more rigidly connected to the inner core 80 using welding or similar expedient.

In a preferred embodiment, an annular planar retention disc 102 is assembled within the annuloplasty ring 70 for securing the suture fasteners 72. The retention disc 102 may be positioned on top of the inner core 80 and within the fabric cover 84, and includes a plurality of apertures for receiving and retaining the suture fasteners 72. By virtue of the retention disc 102, the suture fasteners 72 may be secured within the annuloplasty ring 70 without using the attachment threads 98. The retention disc 102 is desirably a polymer, such as Delrin.

FIGS. 4A-4C are enlarged and sectional views showing an exemplary tubular side entry fastener 110 and a retention pin 112 isolated from the cardiac implants for clarity. The retention pin 112 has a proximal gripping portion 113 and a distal hypotube 114 that resides within and maintains the fastener 110 open, and when removed, permits the fastener to clamp onto the sutures, as will be explained. The illustrated fastener 110 is particularly well-suited to receiving a retention pin 112 as shown, though other retention members such as bifurcated clips, flexible cables, staples, etc. may be used. The term, "retention member" is used herein to refer to these variants, though retention pin may be used for the sake of clarity.

The suture fastener 110 is preferably formed from an elastic material such as a memory material like Nitinol having a collapsible wall structure comprising a pair of tabs 116 cut into a tubular outer wall 118 each of which extends into an inner lumen in the closed state. Each suture fastener 110 further includes a window 120 in the tubular outer wall 118 opposite each of the tabs 116 and into which the respective opposed tab extends in the closed state of the fastener. More particularly, an upper tab 116a extends into an upper window 120 that is opposite from the upper tab. A lower tab 116b extends into a lower window that is formed in the upper tab 116a and not visible in the drawings. The lower window resembles a similar window 122 formed in the lower tab 116b (as shown in an alternative configuration of the tubular fastener in FIG. 4D).

The suture fastener 152 may be formed from suitable biocompatible material, including, for example, Nickel-Titanium or other shape-memory alloys, stainless steel, titanium, other metals, various plastics, and other biologically-compatible materials. The axial height of the suture fastener 110 may be up to about 3 mm. The diameter of the tubular wall 118 may vary depending on suture size, but is typically between about 1-2 mm. Braided sutures are used to attach prosthetic heart valves to annuluses as opposed to monofilament polypropylene sutures (e.g., Prolene) which are used in other surgical environments. In the United States, suture diameter is represented on a scale descending from 10 to 1, and then descending again from 1-0 to 12-0. A number 9 suture is 0.0012 in (0.03 mm) in diameter, while the smallest, number 12-0, is smaller in diameter than a human hair. Although suture size depends on surgeon preference, typically 1-0 or 2-0 braided sutures are used. In one embodiment, if 1-0 sutures are used the diameter of the suture fastener 110 is approximately 1.5 mm, while if 2-0 sutures are used the diameter is 1.0 mm.

Two rows of small holes 124 are provided around the circumference of the outer wall 118 adjacent the proximal and distal ends thereof for suturing the fastener 110 to a cardiac implant. Alternatively, a retention disc such as shown at 54 in FIG. 2B or at 102 in FIG. 3B may be used to secure the fastener 110 to the cardiac implants. Still further, FIG. 4D illustrates an alternative tubular side entry suture fastener 125 that is in most respects similar to the fastener 110, but includes an upper flange 126 wider than the tubular body and sized to retain the fastener 124 on the cardiac implant. That is, sutures are anchored to the anatomical structure below the implant, and pass upward through the suture fastener 124. By virtue of the width of the flange 126, the fastener 124 is prevented from pulling through the cardiac implant, and thus the implant is effectively sandwiched between the anatomical structure and the flange 126. Alternatively, a plurality of suture holes 128 may be provided in the flange 126 to supplement the attachment.

Each of the fasteners 110 receives a hypotube 114 on the retention pin 112 in its lumen to hold the resilient tabs 116 outward into their open state. In this regard, each retention pin 112 is preferably pre-assembled and packaged along with the cardiac implant to avoid the process of connecting each of the retention pins to an associated fastener in the operating room. The hypotube 114 has an outer diameter that is slightly smaller than the inner diameter of the tubular wall of the suture fastener 110, and as such, when inserted in the lumen, the hypotube maintains the tabs 116 flexed outward (straightened) in the axial positions shown in FIG. 4A. Implant attachment sutures 132 may then be passed through an axial opening 134 in the fastener 110 and through an axial slot 136 in the retention pin 112. As mentioned previously, the axial opening 134 and axial slot 136 line up, as in FIG. 4C, and both are aligned with the corresponding slit formed in the sealing ring or sealing edge of the cardiac implant (such as slit 32 seen in FIG. 1A).

It should be noted that forming the hypotube 114 of the retention pin 112 to be tubular with an axial slot 136 leading to an inner lumen is only one way to ensure that a suture can enter the lumen of the fastener 110. That is, other configurations include a semi-cylindrical hypotube 114 that occupies space within the fastener 110 to hold the tabs 116 outward while still leaving space for sutures within the fastener lumen. Various configurations are possible, the requirement being only that be hypotube 114 is other than solid and cylindrical.

The hypotube 114 is desirably made of surgical grade metal such as stainless steel so that it maintains its diameter against the inward force of the fastener tabs 116 over potentially long periods of storage time. Further, a metal will better resist gouging by the tabs and can therefore be easily removed from within the fasteners 110. It will be understood by the reader that the hypotube 114 cannot simply be inserted downward through the fastener 110, but instead a thin assembly shaft (not shown) of the same size is first inserted upward to force the tabs 116 outward. Subsequently, the hypotube 114 is pushed downward through fastener 110 so as to displace the assembly shaft without permitting the tabs 116 to spring inward. This can be done manually, but preferably a loading fixture to center the cooperating elements is used. An exemplary loading fixture will be described below.

In use of the suture fastener 110, as seen in FIGS. 4A and 4B, the tabs 116 are spring-biased inward and, upon removal of the hypotube 114, clamp onto and restrict distal (downward) movement of a suture 132 through the fastener without preventing proximal (upward) movement. That is, the tabs 116 in the closed state permit distal (downward) movement of the cardiac implant on the sutures while preventing proximal (upward) movement. Consequently, whether deployed or not, the suture fasteners 110 permit a user to parachute a cardiac implant down an array of pre-installed sutures until the implant sits on the annulus, at which point the suture fasteners prevent the implant from moving upward from the annulus.

Another option for the suture fasteners disclosed herein (such as the tubular fastener 110) is to provide a plastically-deformable portion in addition to the spring-biased tabs. For example, the upper end of the tubular wall 118 of the suture fastener 110 could be formed of material that is capable of plastic deformation. A crimping tool or other such device can then be lowered to the implant site and used to flatten the top end of the fastener on the anchoring sutures 132 to supplement the spring-biased tabs 116.

FIGS. 5A and 5B show the tubular side entry fasteners 110 embedded in a sealing ring 140 of a prosthetic heart valve 142, before and after deployment. That is, the retention pins 112 are initially in place within the fasteners 110, as in FIG. 5A. Pulling the retention pins 112 upward deploys the tabs 116 in the fasteners 110, thus engaging the sutures 132. To help avoid a multitude of small retention pins 112 in the surgical site, one or more may be coupled together with tethers or sutures 144. For example, every three of the retention pins 112 may be coupled together so that they are much less likely to be misplaced.

In one preferred sequence, the surgeon advances the cardiac implant (such as heart valve 142) until it seats at the target annulus. During this advancement, the free ends of all of the attachment sutures 132 are controlled to prevent slack. Once the cardiac implant reaches the target annulus, the surgeon applies a desired amount of tension to each pair of the attachment sutures 132, and simultaneously displaces the corresponding retention pin 112 in a proximal direction, as seen in FIGS. 4B and 5B to deploy the fasteners 110. Each pair of attachment sutures 132 is then severed close to the proximal end of the respective suture fastener 110. This can be done with scissors, sheared by the retention pin 112 (e.g., between the end of the tube and the suture fastener 110), sheared by a sharp edge provided on the suture fastener 110 (not shown), or any combination thereof.

FIGS. 6-9 illustrate an exemplary assembly configuration for a prosthetic heart valve having the side entry tubular fasteners disclosed herein. FIG. 6 is an exploded perspective showing an inner stent member 150 above an annular retention disc 152 which, in turn, is above an annular sealing ring sponge 154. Again, the annular retention disc 152 may be planar, as shown, or have an undulating contour to match the contour of the sponge 154 which, in turn, is shaped to better match the anatomy such as the aortic annulus. The stent member 150 defines an undulating shape having upwardly projecting commissure posts 156 in between downwardly arcing cusps 158. In preferred embodiments, the stent member 150 includes a polymer inner band 160 which defines the commissure posts 156, and a metallic outer band 162 which matches the shape of the inner band except for being truncated short of the top of the commissure posts. The sponge 154 may be formed of any pliant material such as silicone or fabric, and serves to provide a soft sealing member surrounding the inflow end of the heart valve to prevent paravalvular leakage. The retention disc 152 features a series of apertures 164 distributed evenly around its circumference and proximate its outer peripheral edge 166. Each of the apertures 164 opens to the peripheral edge 166 through a short channel 168.

FIG. 7A is a perspective view of the retention disc 152 having the apertures 164 around its periphery. A series of assembled side entry fasteners 110 and retention pins 112 are shown being inserted into the apertures 164. As mentioned above, the vertical slits in the side of the fasteners 110 and hypotubes 114 align and are oriented so as to register with the channels 168 in each of the apertures 164. In this regard, anti-rotation structures may be provided on the fasteners 110, pins 112, and apertures 164 to ensure that these side openings align. For example, a flat portion extending the length of the hypotube 114 may register with a flat within the lumen of the fastener 110, and the exterior wall of the fastener may include a flat that registers with a similar flat formed in the corresponding aperture 164. Alternatively, ribs and channels may be formed on the opposing faces of these components. Of course, those of skill in the art will understand that there are a number of ways to ensure rotational registration of the side openings.

FIG. 7B shows the retention disc 152 of FIG. 7A above the sealing ring sponge 154 with the tubular fasteners 110 extending within outer recesses 170 formed within the sponge. With reference back to FIG. 6, the sponge 154 features a series of the grooves or recesses 170 evenly distributed around its periphery and opening both to its upper face and its outer wall. The outer diameter of the retention disc 152 is approximately equal to the outer diameter of the sponge 154, such that the downwardly projecting fasteners 110 fit closely within the recesses 170.

Next, FIG. 7C shows the components from FIG. 7B with a tubular fabric piece 172 disposed within the annular sponge 154. The fabric piece 172 features a series of axial slits 174 formed in both its upper 176 and lower 178 edges. The fabric piece 172 is then wrapped around the top and bottom of the assembled retention disc 152 and sponge 154 and sewn thereto. The slits 174 enable the fabric to go between the upstanding retention pins 112.

FIG. 7D illustrates a stent subassembly 180 including the components shown exploded in FIG. 6 covered and joined together with fabric. More particularly, the structure formed by wrapping the fabric piece 172 around the assembly in FIG. 7C defines a sealing ring 182. The stent member 150 from FIG. 6 is then covered with fabric and attached to the inner wall of the sealing ring 182.

Now with reference to FIG. 8, a leaflet subassembly 190 comprises a fabric-covered undulating wireform 192 having flexible leaflets 194 attached thereto. The wireform 192 defines narrow arcuate upwardly-projecting commissure regions 196 in between downwardly-projecting arcuate cusp. The leaflets 194 extend inward from the surrounding wireform 192 into a flow orifice defined thereby. In a preferred embodiment, there are three bioprosthetic leaflets 192 that curve toward the outflow direction and "coapt" in the middle of the valve orifice to ensure one-way flow through the valve. FIG. 8A is a sectional view through one edge of the leaflet subassembly showing a fabric covering 200 around the wireform 192 that extends outward thereon and is folded into a sewing tab 202. The outer edge 204 of each of the leaflets 194 extends under the sewing tab 202 and may be initially sewn thereto and, as seen in FIG. 9A, is then sandwiched and sewn between the sewing tab 202 and a sewing tab 206 at the upper end of the fabric-covered stent member 150.

FIG. 9 illustrates a completed prosthetic heart valve 210 having the tubular side entry fasteners and corresponding retention pins 112 around the periphery of the sealing ring 182. The small vertical slits 212 in the outer edge of the sealing ring 182 are formed by the slits 174 in the fabric piece 172 of the sealing ring (see FIG. 7C). The slits 212 are located at the circumferential location of the fasteners 110, which, though not shown, are positioned in the recesses 170 of the sealing ring sponge 154.

FIG. 9A is a sectional view through the heart valve 210 showing the position of one of the tubular side entry fasteners 110 within the sealing ring 182. The slit 212 is indicated by fabric that may be wrapped around the inside walls of each of the recesses 170. Alternatively, the slits may be left alone on the outer extent of each of the recesses 170, so that the sectional view would show an outer portion of the sponge 154. There are various ways to wrap the fabric piece 172 around the sponge 154, as long as a slit or opening is left leading to the fastener 110.

Finally, FIG. 9B is an enlarged view of one of the side entry fasteners 110 and its accompanying retention pin 112 looking directly radially inward through the vertical slit in the sealing ring 182. It should be noted that the retention pin 112 also includes an axial slot 214 so that the attachment sutures 132 can be passed to the interior of the entire structure.

The present application also contemplates a side-entry suture fastener 250 that has bifurcated clamping halves, as shown in FIGS. 10-15.

Figure 10A:
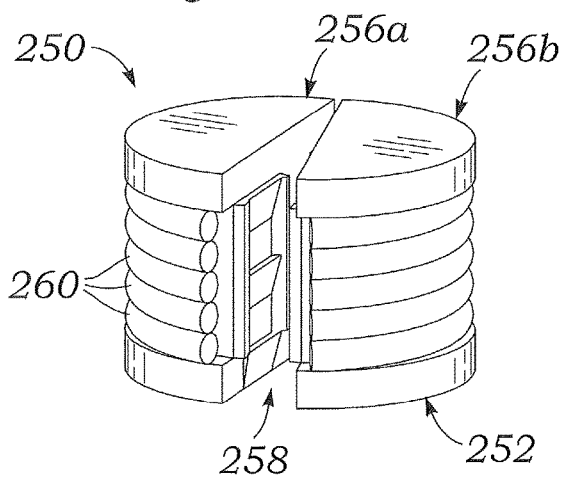
FIGS. 10A and 10B are perspective views of an alternative split "side entry" suture fastener having a bifurcated locking clamp with an axial hinge biased closed by exterior C-springs.
Figure 10B:
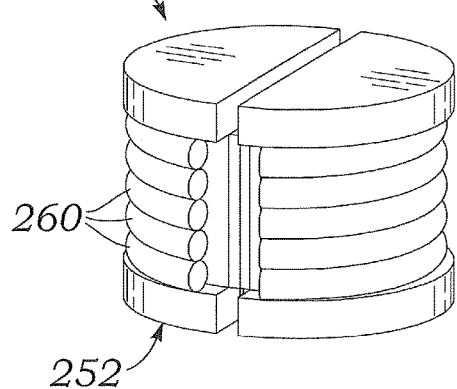
Figure 12:
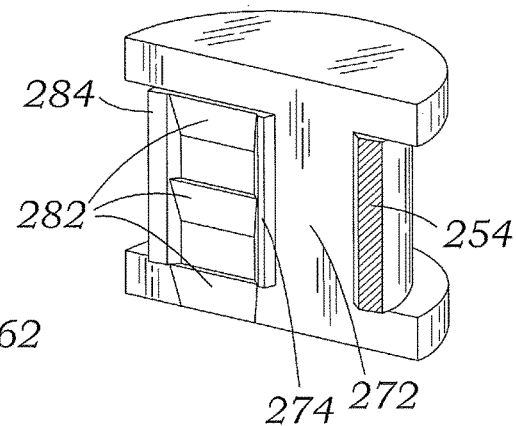
FIG. 12 shows an inner wall structure of one half of the clamp.

With reference to FIGS. 10A and 10B, the fastener 250 provides a suture locking retainer which eliminates the need for tying knots in surgical sutures. The suture fastener 250 includes a bifurcated locking clamp 252 having an axial hinge 254, as seen in FIG. 12. The locking clamp 252 can be plastic and molded, and has two substantially identical halves 256a, 256b separated by a variable-sized slot 258. The two halves 256a, 256b are biased together by at least one exterior "C" clip 260. The axial hinge 254 is desirably a "living hinge" formed in the molded part along one side so that the halves 256a, 256b can pivot apart to vary the size of the slot 258 and form an opening on the side opposite from the hinge in which sutures can be inserted. Alternatively, a true hinge may be provided between the two halves 256a, 256b.

As with the earlier embodiments, an overall exemplary size of the device can be 2 mm in height and diameter, or smaller. The initial design shown here is based on 2-0 sutures, which are commonly used in valve replacement procedures. Furthermore, the dimensions and parameters for materials described above for the earlier embodiments also apply to the fastener 250 of FIGS. 10-15.

Figure 11:
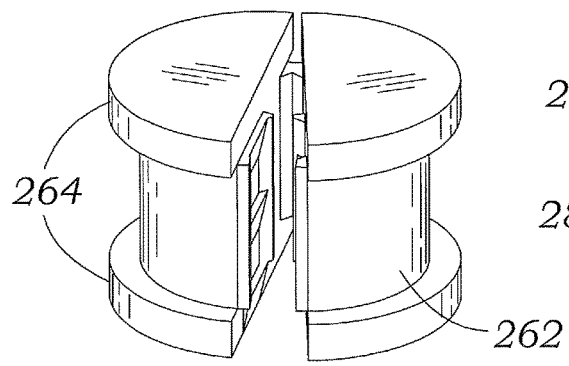

As seen in FIG. 11, each half 256 includes a semi-cylindrical middle recess 262 between two outwardly-projecting end flanges 264. When the two halves 256 are brought together, they define a spool shape. As seen in FIGS. 10A, 10B, the C-clips 260 are received in the recess 262 with their open ends 266 flanking the variable-sized slot 258 and directly opposed to the hinge 254. The end flanges 264 hold the C-clips 260 in place.

Figure 13A:
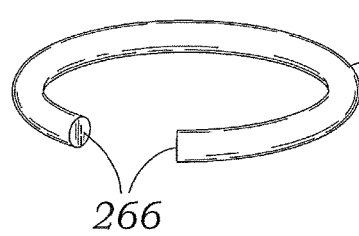
FIG. 13A shows one of the C-springs.

One or more of the C-clips 260 seen in FIG. 13A are placed around the clamp and sized such that they apply a force which acts to close the clamp 252 and close or eliminate the slot 258, thus clamping onto sutures that pass through the slot. The C-clip(s) 260 thus provide biasing members positioned on the outside of the locking clamp 252 having a relaxed size that, in the absence of any other object in the slot 258, urges the inner surfaces of the clamp halves 256 together such that the slot has a width smaller than the suture thickness. In an alternative configuration, a section of tube with a slit (forming a "C" in cross section) could replace the array of "C" clips. Indeed, the term, "biasing member" should be understood to refer to one or more elements as described herein.

The C-Clips 260 would most likely be formed from Nitinol wire, although other materials such as stainless steel should not be excluded. For the exemplary embodiment shown, the C-clips 260 are formed from 0.008" diameter wire and have an outside diameter of 0.079" (2 mm). The illustrated embodiment incorporates five C-clips 260, though additional C-clips 260 could be added to increase the clamping force. Additionally, the clamping force can be increased significantly by small increases in the wire diameter of the C-clips 260. The bending stiffness of a circular wire is proportional to the 4th power of its diameter, and so increasing the wire diameter from only 0.008" to 0.010" increases the clamping force by a factor of 2.4, while an increase to 0.012" would result in a five-fold increase in clamping force. Thus by changing the number of C-Clips and their wire diameters, large changes in the clamping force can be realized with minimal impact on the device diameter and small changes in device height.

Figure 13B:
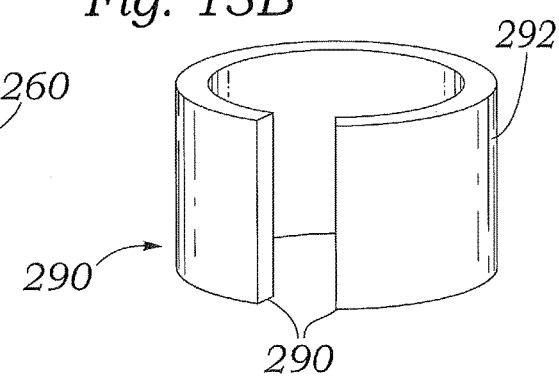
FIG. 13B shows an alternative C-clip in the form of a split tube.

FIG. 13B shows an alternative biasing member or C-clip 290 in the form of a short tubular collar 292 having an axial split on one side terminating in free ends 294 separated across a slot or gap. The cross-section of the collar 292 is a C-shape, and the axial height is desirably about the same as the height of the stack of C-clips 260 seen in FIG. 10B, or the distance between the end flanges 264 of the bifurcated locking clamp 252 as seen in FIG. 11. The C-clip 290 is also desirably made of Nitinol (binary alloy of primarily Nickel and Titanium), though NiTiCo (ternary alloy of primarily Nickel, Titanium and Cobalt) is stiffer than "regular" Nitinol and hence allows a smaller overall diameter and height of the device.

The NiTiCo is up to about 80% stiffer than Nitinol, so the math shows that the diameter of the NiTiCo collar can be about 21% less to achieve the same force (because force roughly goes with wall thickness to the $3^{rd}$). As an example, that could reduce the OD of the collar from 2.0 mm for Nitinol to 1.58 mm for NiTiCo. Or, for the same diameter the NiTiCo collar could be ~80% shorter, since the force is linear with length.

FIGS. 14A-14D illustrate a sequence of operation of the side entry suture fastener 250. First, the assembled fastener 250 includes the aforementioned components as well as a retention pin 270 having an upper head 271 (again, the term "retention pin" should not be considered limiting, and is shorthand for a more generic "retention member."). Prior to use, the two halves 256a, 256b are forced apart so that the retention pin 270 may be inserted into a retention pin channel 272, as seen best in FIG. 12. The retention pin channel 272 is defined between the axial hinge 254 and an axially-oriented retainer rib 274 formed on one or both halves 256 and extending into the slot 258. Release of the two halves 256 permits the C-clips 260 to force the two halves to pivot toward one another and clamp onto the retention pin 270. Preferably, the fastener 250 is pre-assembled by the manufacturer, i.e. the retention pin 270 and C-clips 260 are pre-assembled with the clamp halves 256a, 256b. The presence of the retention pin 270 holds open the two halves 256a, 256b so that the slot 258 widens into the opening opposite the hinge 254 into which one or more sutures 280 can be inserted.

As a first step in the process of deployment, the surgeon laterally displaces one or more sutures 280 toward one of the suture locking devices 250, as seen in FIG. 14A (and as depicted for the first embodiment in FIG. 1A). As mentioned, the slot 258 defines an opening into which the sutures 280 are received. As seen in FIG. 14B, the surgeon then tensions the sutures 280 while the prosthetic heart valve sealing ring or annuloplasty ring to which the fastener attaches is seated against the native annulus. In FIG. 14C, the retention pin 270 is removed, thus allowing the C-clips 260 to force closed the opposite halves 256a, 256b of the clamp 252, thus clamping the suture(s) 280 therebetween, as seen in FIG. 14D.

Alternatively, as mentioned above, the fastener 250 may be deployed prior to the valve or annuloplasty ring being advanced to the annulus, as the exemplary fastener permits one-way travel of the sutures therethrough. With reference back to FIG. 12, the inner faces of one or preferably both of the device halves 256a, 256b include a plurality of grip members 282 that help prevent relative movement between the deployed fastener 250 and the sutures 280. More particularly, the grip members 282 prevent relative longitudinal movement between the fastener 250 and sutures 280 in only one direction. For example, the grip members 282 are formed as wedges with a ramp angled in one axial direction, in the illustrated embodiment the wedges are angled upward. Due to their orientation, and after the fastener 250 has been deployed, the sutures 280 would be prevented from moving relatively downward, but could be pulled through upward. Stated another way, the fastener 250 could be slid downward on the sutures, but not upward. This configuration enables the surgeon to increase the tension on the sutures 280 once the fastener 250 is closed, but loosening of the sutures would be inhibited. Desirably, both inner faces of the device halves 256a, 256b include an axial bar 284 that helps retain the sutures 280 within the slot 258. As seen in FIG. 14D, the bars 284 extend sufficiently inward toward each other so as to close and present a barrier to lateral escape of the sutures 280.

FIG. 15 illustrates how the suture(s) 280 can be tensioned further after deployment of the fastener 250. It will be noted that only one suture 280 is shown in this view to emphasize that one or more can be secured by the fastener 250. The individual grip members 282 could be axially offset on the two halves 256a, 256b to enhance their frictional hold on the suture(s) 280. In other words, deploying the fastener 250 creates a serpentine path for the suture(s) 280 between the alternating grip members 282. The cross-section of the slot 258 shows the offset suture grips 282, which thus act as a "one way" ratchet that allows for further tensioning of the suture(s) after deployment of the device, but resist loosening of the sutures.

Figure 16A:
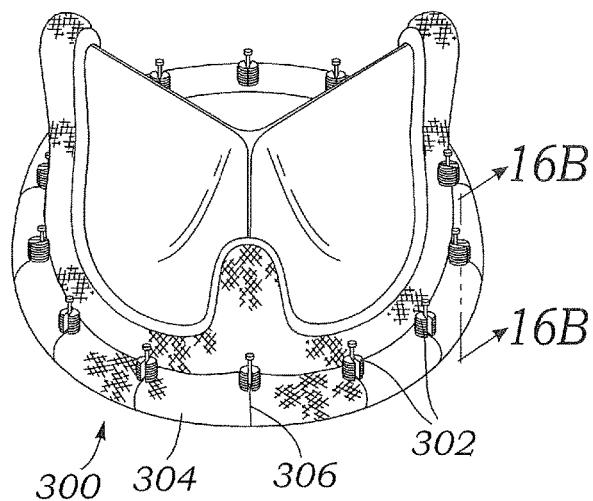
FIG. 16A is a perspective view of a flexible leaflet prosthetic heart valve having a number of the split side entry fasteners distributed around its sealing ring which has vertical slits at the circumferential location of each one of the fasteners.
Figure 16B:
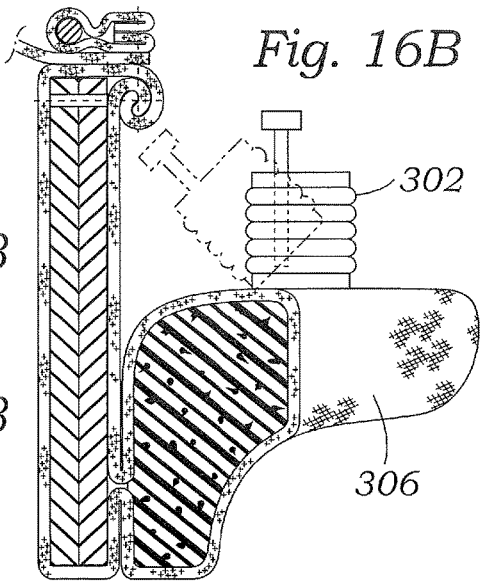
FIG. 16B is a sectional view through the prosthetic heart valve of FIG. 16A showing the position of one of the tubular side entry fasteners on top of the sealing ring.

FIG. 16A is a perspective view of a flexible leaflet prosthetic heart valve 300 having a number of the split side entry fasteners 302 distributed around its sealing ring 304. Each of the fasteners 302, as seen in the sectional view of FIG. 16B sits on top of the sealing ring 304, rather than being embedded within. Although not shown, the fasteners 302 may be secured to the sealing ring 304 with sutures, adhesives, or other similar expedient. The sealing ring 304 is configured as described above to have vertical slits 306 at the circumferential location of each one of the fasteners 302. As seen in FIG. 16B, each fastener 302 is positioned to extend partly over the corresponding slit 306 so that sutures can be laterally displaced through the slit 306 and into the slot within the fastener. Positioning the fasteners 302 partly over the slit 306 and partly over a solid portion of the sealing ring 304 helps prevent the fastener from being pulled through the slits.

Figure 17A:
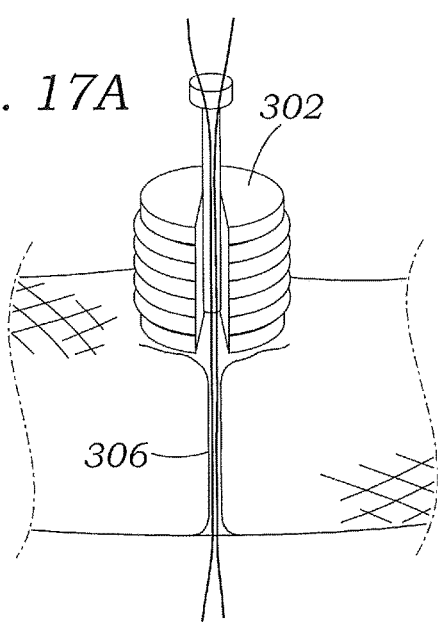
Figure 17B:
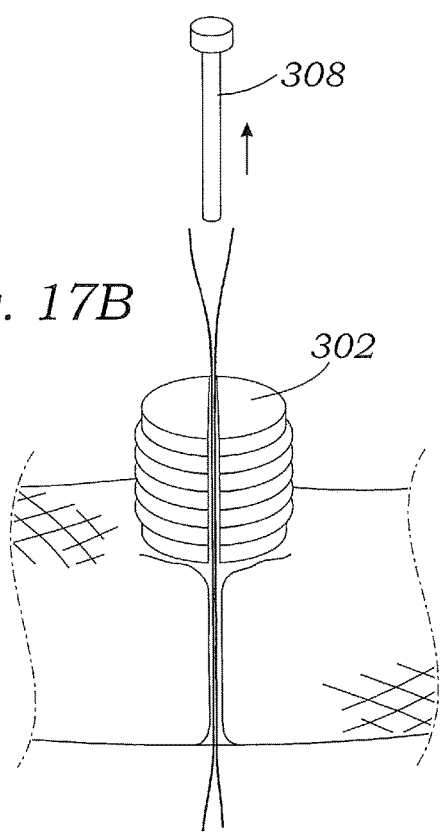
FIG. 17B shows the fastener after deployment by removal of a retention pin.

FIG. 17A is an enlarged view of one of the side entry fasteners 302 looking directly radially inward through the vertical slit 306 in the sealing ring 304 and prior to deployment, while FIG. 17B shows the fastener 302 after deployment by removal of a retention pin 308. It will be appreciated that the sealing ring 304 is also representative of annuloplasty ring.

In an alternative embodiment depicted in phantom in FIG. 16B, each of the fasteners 302 sits on top of the sealing ring 304 and is attached only on a radially inner corner such that it can be pivoted upward; i.e., the fastener 302 behaves as if it was hinged to the sealing ring 304 at its bottom inner corner (opposite the opening in the fastener). When pivoted upward, a pair of sutures could be placed through the slit 306 in the sealing ring 304 adjacent to the flipped-back fastener 302, and then the fastener is then hinged back flat against the sealing ring, capturing the sutures.

Figure 18A:
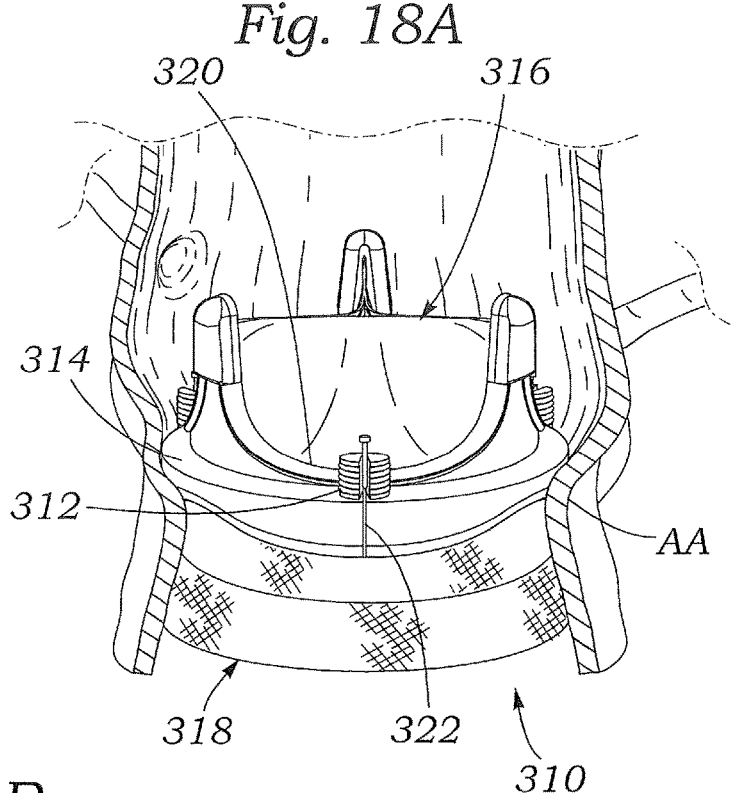
FIG. 18A is a perspective view of a hybrid prosthetic heart valve with a cloth-covered anchoring skirt expanded against a subvalvular wall below an aortic annulus and illustrating three of the split side entry fasteners positioned above a sealing ring thereof.

FIG. 18A is a perspective view of a hybrid prosthetic heart valve 310 implanted at an aortic annulus AA and illustrating three of the split side entry fasteners 312 positioned above a sealing ring 314. The fasteners 312 may be attached to the sealing ring 314 as described above. The aortic prosthetic heart valve 310 is a hybrid type with a valve member 316 having an expandable anchoring skirt 318 attached to and projecting from an inflow end of the valve below the aortic annulus AA. A balloon catheter may be used to expand the anchoring skirt 318 against the surrounding sub annular tissue. Of course, other expansion devices may be used, and the skirt 318 is thus termed "plastically-expandable" to encompass various ways of expansion.

Further details of such a hybrid prosthetic heart valve 310 and an associated delivery system can be found in U.S. Patent Publication No. 2012/0065729 to Pintor, et al., filed Jun. 23, 2011 and expressly incorporated herein. In the Pintor disclosure, three guide sutures are pre-installed at the aortic annulus and threaded through cusp regions of the prosthetic heart valve. The three guide sutures are primarily used to orient the heart valve rotationally within the aortic annulus such that the leaflets register with the surrounding coronary ostia (in two of the three coronary sinuses). However, the guide sutures also supplement the anchoring function of the expandable anchoring skirt 318. There remains a problem of the time it takes to tie off each of the three guide sutures, which problem is alleviated by the side entry knotless suture fasteners 312, as described in the present application.

Figure 18B:
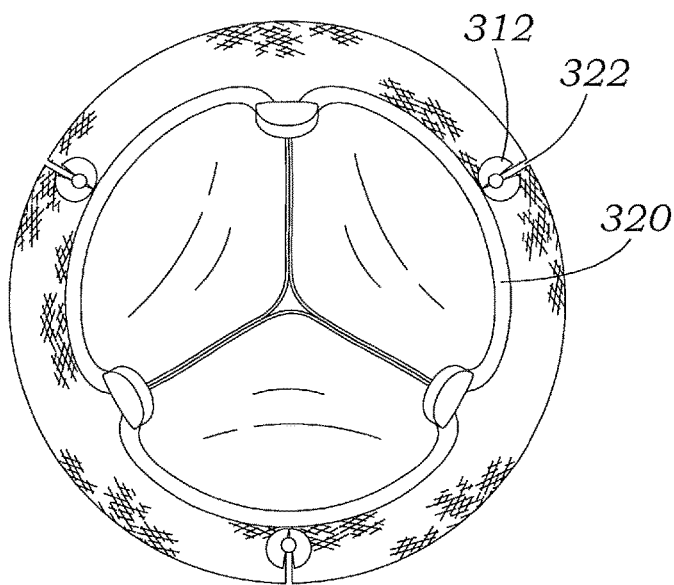
FIG. 18B is a top plan view of the prosthetic heart valve showing distribution of the split fasteners at the valve cusps.

FIG. 18B is a top plan view of the prosthetic heart valve showing distribution of the split fasteners 312 at the valve cusps 320. There are desirably three suture fasteners 312 on the sealing ring 314 located in the middle of the valve member cusps 136. Each of the side entry fasteners 312 is circumferentially aligned with a slit 322 formed in the sealing ring 314, such as described above for other embodiments. Preferably, the sealing ring 314 has a relatively flat or constant elevation proximal (outflow) face, and an undulating distal (inflow) face that is shaped to match the undulating contour of the aortic valve annulus. In the middle of the cusps 320, the sealing ring 314 has a maximum thickness which provides more material for securing anchoring sutures with the suture fasteners 312.

The heart valve 310 is mounted on a holder and handle assembly and the three pairs of anchoring sutures are inserted through the slits 322 such that they may be engaged by the fasteners 312. The valve 310 is then advanced down the anchoring sutures until the distal face of the sealing ring 314 contacts the aortic annulus AA, in the position shown in FIG. 18A. The prosthetic heart valve sealing ring 314 seats on the inwardly projecting supra-annular shelf of the aortic annulus AA, and the anchoring skirt 318 is expanded by the balloon catheter in the subannular region. Each pair of anchoring sutures can be properly tensioned by the surgeon just prior to converting the suture fasteners 312 from their open states to their closed states. Alternatively, the fasteners 312 are capable of sliding down the anchoring sutures after being deployed and prevent the valve from pulling upward away from the annulus.

Figure 19:
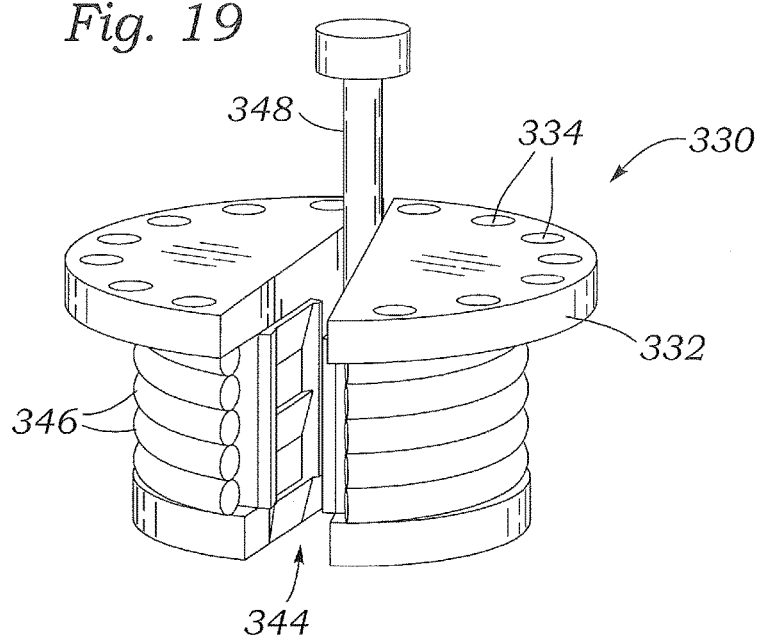
FIG. 19 is a perspective view of an alternative split side entry fastener having an enlarged upper flange with sewing holes therein.
Figure 20A:
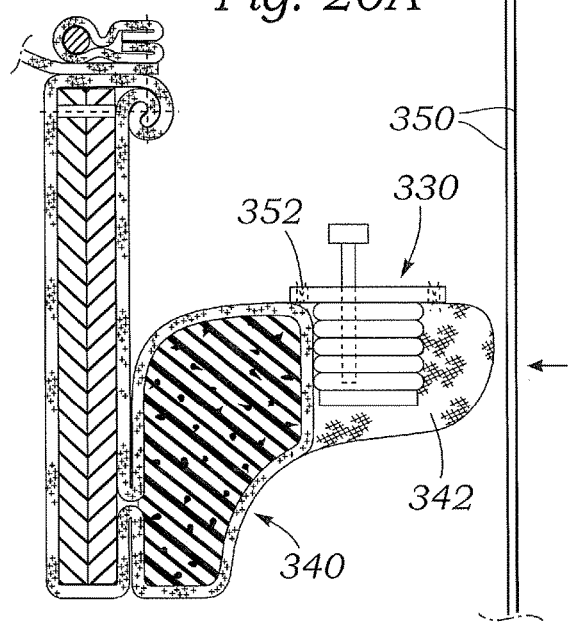
FIGS. 20A and 20B are sectional views through a prosthetic heart valve having one of the side entry fasteners of FIG. 19 embedded in a sealing ring therein before and after deployment.
Figure 20B:
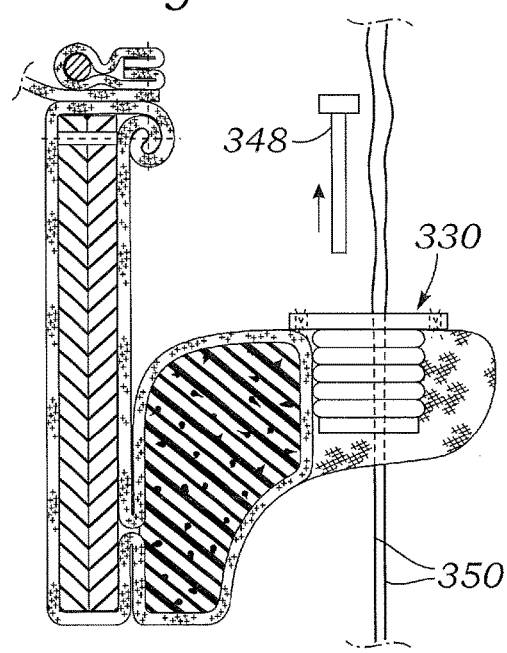

FIG. 19 is a perspective view of an alternative split side entry fastener 330 having an enlarged upper flange 332 with sewing holes 334 therein. As seen in FIGS. 20A and 20B, the side entry fasteners 330 maybe embedded in a sealing ring 340 of a heart valve, similar to those described above. Alternatively, the sealing ring 340 is representative of the sealing edge of an annuloplasty ring.

As described above, the sealing ring 340 features a plurality of radial slits 342 therein which opened to the variable-sized mouth 344 of the bifurcated fastener 330. As before, a plurality of C-clips 346 bias the two halves of the bifurcated fastener 330 toward each other, and a retention pin 348 maintains the mouth 344 open for introduction of anchoring sutures 350. A sequence of displacing the anchoring sutures 350 into the slit 342 and within the mouth 344 of the fastener 330 followed by removal of the retention pin 348 is shown in FIGS. 20A and 20B. Stitches 352 through the sewing holes 334 may be used to secure the upper flange 332 of the fastener 332 the sealing ring 340. Alternatively, the flange 332 may be solid without the sewing holes and be wide enough to prevent the fastener from pulling through the slit 342.

FIGS. 21A-21D illustrate several components and steps in assembling a prosthetic heart valve 360 having the embedded side entry fasteners 330 of FIGS. 19-20. In FIG. 21A, an annular, pliant sponge 362 similar to those described is shown exploded from a tubular fabric piece 363. The fabric piece 363 has a plurality of vertical slits 364 therein each of which correspond to a recess 366 in the outer edge of the sponge 362.

FIG. 21B shows the sponge 360 and fabric piece 363 assembled into a sealing ring 368, wherein the fabric piece has been wrapped around the sponge and sewn thereto. Each of the slits 364 is seen on the outer edge of the sealing ring 368. A plurality of the side entry fasteners 330 are shown elevated above the sealing ring 368, with dotted lines indicating that they will be inserted through the slits 364 to fit in the recesses 366 of the sponge 362. The upper flanges 332 of the fasteners 330 remain on top of the sealing ring 368, and may be attached thereto with sutures as explained above. Tethers 370 are shown connecting the retention pins 348 of the three fasteners 330 shown.

FIG. 21C shows the completed sealing ring 368 having the fasteners 330 embedded around its periphery. As shown, there are tethers 370 connecting the retention pins 348 of each of the three fasteners 330, and there are a total of 18 fasteners. Of course, the number of fasteners 330 can be adjusted, and the tethers 370 can connect any number of retention pins 348, the number shown being exemplary only.

FIG. 21C also shows a cloth-covered stent member 374 above the sealing ring 368, with a wireform subassembly 376 above that. Connecting these components as was described earlier results in the assembled heart valve 360 seen in FIG. 21D. Providing the tethers 370 connecting at least two of the fasteners 330 helps reduce the possibility of losing one of the retention pins 348. That is, as the retention pins 348 are removed from the fasteners 330, they are tethered to other of the pins so as to be more difficult to misplace.

Figure 22:
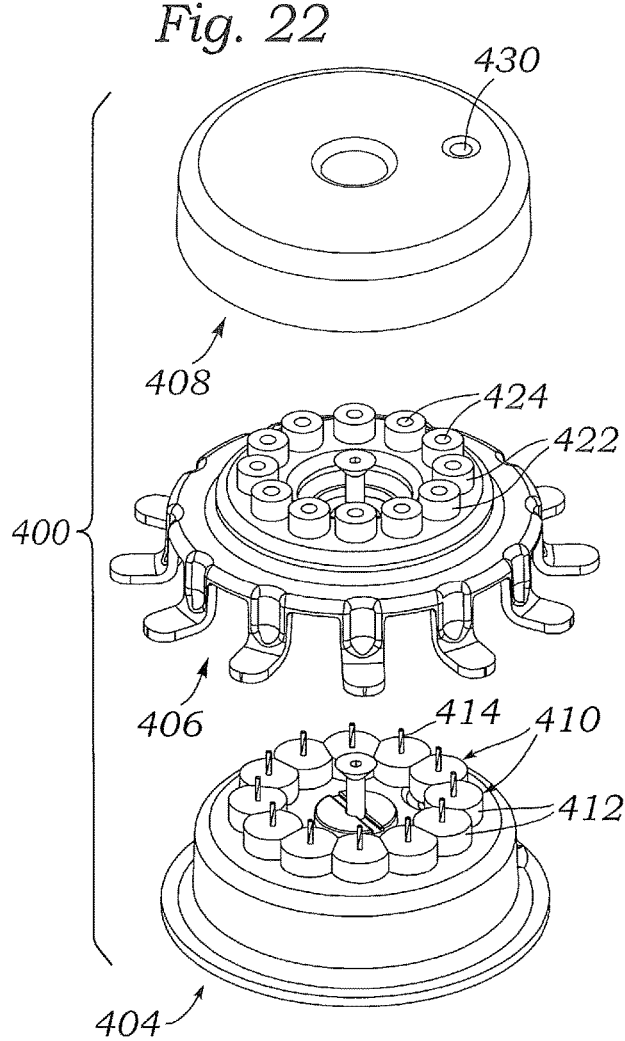
FIG. 22 is a perspective exploded view of an exemplary multiple suture fastener loading fixture of the present application.
Figure 23:
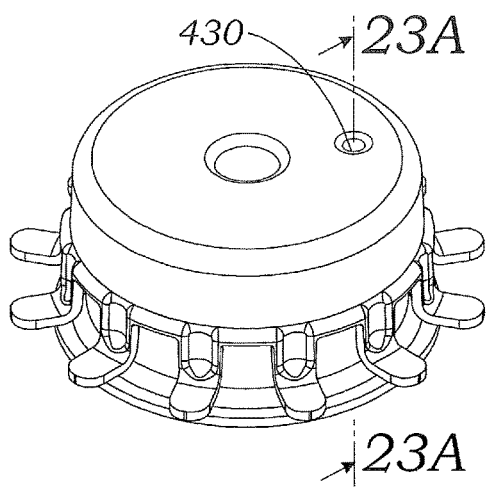
Figure 23A:
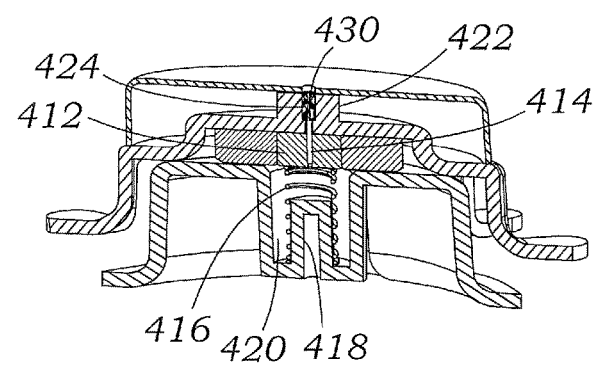
FIG. 23A is a sectional view through one of a plurality of load stations therein.

FIGS. 22,23 and 23A illustrate an exemplary suture fastener loading fixture 400 of the present application capable of rapidly loading a number of the suture fasteners 110 of FIGS. 4-9 onto the corresponding retention pins 112. In the illustrated embodiment, there are 12 load stations in the loading fixture which may be sufficient to secure a surgical heart valve or an annuloplasty ring to an annulus. Of course, more or fewer load stations may be provided in the fixture 400 depending on the application.

The loading fixture 400 includes a lower base member 404, an intermediate platform 406, and an upper cover 408 rotatable about the platform. The base member 404 defines a plurality of load stations 410 circumferentially spaced around a central axis, each including independently moving blocks 412 having thin mandrels 414 projecting upward therefrom. As seen in the sectional view of FIG. 23A, each block 412 is supported from underneath by a spring 416 centered over a spindle 418 in a cavity 420 of the base member 404. Each load station 410 further includes a cylinder 422 on the intermediate platform 406 centered over the block 412 and mandrel 414. As seen in FIG. 23A, each cylinder 422 defines a receptacle 424 over a through hole (not numbered) sized so that the mandrel 414 projects upward from the block 412 into the receptacle. The mandrel 414 has an outer diameter that is approximately equal to the luminal diameter of the suture fasteners 110, and the receptacles 424 have an axial height slightly greater than the length of the suture fasteners, such that the load stations 410 can each be loaded with a suture fastener on the mandrel and within the receptacle, as seen best in FIG. 25A.

The intermediate platform 406 and upper cover 408 are secured over the base member 404 using a central bolt 426. Removal of the bolt 426, upper cover 408, and intermediate platform 406 exposes the plurality of upstanding mandrels 414 onto which suture fasteners 110 can be manually placed. The intermediate platform 406 goes over the base member 404 and the two are keyed together to prevent relative rotation. The upper cover 408 is then secured over the intermediate platform 406 with the bolt 426. The upper cover 408 cooperates with the intermediate platform 406 for step-wise rotation thereover, as will be described.

Each load station 410 further includes a lead-in cavity 430 formed in the upper cover 408 as seen in FIGS. 23/23A sized to closely receive the retention pins 112. Preferably, there is only one lead-in cavity 430 in the cover 408 which the user can rotate around the axis of the generally cylindrical loading fixture 400 to register with different load stations 410. In the illustrated embodiment the lead-in cavity 430 defines a gradual inward taper to help center the distal end of the retention pins 112.

FIG. 24 is a perspective view of the loading fixture 400, while FIGS. 25 and 25A are sectional views through the load station 410 showing a retention pin 112 entering the lead-in cavity 430. The hypotube 114 projects distally from the pin 112 prior to loading with a suture fastener. As will be shown, inserting the retention pin 112 into each load station 410 enables transfer of one of the suture fasteners 110 to the hypotube 114.

FIGS. 26A-26C illustrates several steps in using the load stations 410 to load a suture fastener 110 onto the retention pin 112. FIG. 26A illustrates the retention pin 112 just prior to bottoming out within the lead-in cavity 430. As mentioned above, the cooperation between the cavity 430 and the distal end of the retention pin 112 desirably centers the projecting hypotube 114 over the load station receptacle 424. A suture fastener 110 is shown within the receptacle 424 mounted on the mandrel 414. The top ends of the suture fastener 110 and mandrel 414 are positioned just below the upper opening to the receptacle 424 such that the upper cover 408 can freely rotate over the tops of the cylinders 422, as seen in FIG. 22. That is, the upper cover 408 is in contact with the flat and substantially continuous tops of the cylinders 422. Desirably, interacting features such as small molded bumps or the like (not shown) are provided in the upper cover 408 and intermediate platform 406 so that the lead-in cavity 430 can "click" from load station 410 to load station in a step-wise manner.

FIG. 26B shows the retention pin 112 bottoming out within the lead-in cavity 430. As mentioned, the projecting hypotube 114 has the same diameter as the mandrel 414, both of which fit closely within the lumen of the suture fastener 110. Prior to FIG. 26B, the mandrel 414 maintains the collapsible wall structure on the suture fastener 110 in an open state. As the hypotube 114 descends, it displaces the mandrel 414 from within the suture fastener 110, pushing the mandrel 414 and the attached block 412 downward against the force of the spring 416. The receptacle 424 has a bottom floor (not numbered) that limits downward movement of the suture fastener 110. Eventually, the hypotube 114 advances just far enough to displace the mandrel 414 from within the fastener. The distance that the hypotube 114 projects from the gripping portion 113 of the retention pin 112 is approximately equal to the height of the receptacle 424 such that the hypotube ends within or at the bottom end of the fastener 110 when the retention pin 112 bottoms out within the lead-in cavity 430.

It should be noted that this loading procedure is necessitated by the one-way nature of the collapsible wall structure on the suture fastener 110. That is, each suture fastener 110 may be easily pushed downward onto the mandrel 414, which forces the collapsible wall structure outward. However, the fasteners 110 could not otherwise be pushed upward directly onto the hypotube 114 because of the configuration of the collapsible wall structure. This will be clear from inspection of the exemplary fasteners 110 as described above with reference to FIGS. 4A-4D, wherein the collapsible wall structure comprises the oppositely-directed tabs 116a, 116b cut into the tubular outer wall 118 and extending into the central lumen in the closed state of the fastener.

In any event, displacing the mandrel 414 from within the fasteners 110 transfers the inward force exerted by the elastic tabs 116 to the hypotube 114, which temporarily secures the fastener onto the retention pin 112. Additionally, after expulsion of the mandrel 414 from the fastener 110, the spring 416 pushes the block 412 and mandrel 414 upward, thus elevating the gripping portion 113 of the retention pin 112 above the level of the cover 408, enabling easy removal. As seen in FIG. 26C, the retention pin 112 may then be lifted free of the load fixture 400 for assembly into a cardiac implant, with the suture fastener 110 held on the projecting hypotube 114.

In one embodiment, the fastener loading fixture 400 includes the same number of load stations 410 as the number of fasteners 110 that will be assembled into the cardiac implant. Furthermore, the loading fixture 400 accommodates multiple fasteners 110 having retention pins 112 that are tethered together, such as described above with reference to FIGS. 21A-21D. That is, the tethers 370 are flexible, enabling the retention pins 112 for a group of tethered fasteners to be manipulated through adjacent lead-in cavities 430, either one at a time or simultaneously. Alternatively, the tethers 370 could be made more rigid such that a plurality of retention pins 112 can be pulled at the same time. However, the distance between the retention pins 112 determined by the length of the rigid tethers 370 would have to be the same as the distance between the fasteners 110 on the cardiac implant as well as the distance between the load stations 410 in the loading feature 400.

While the invention has been described in its preferred embodiments, it is to be understood that the words which have been used are words of description and not of limitation. Therefore, changes may be made within the appended claims without departing from the true scope of the invention.

What is claimed is:

1. A method of securing a cardiac implant to a heart valve annulus, comprises:
providing a pre-assembled cardiac implant system including an implant defining a flow orifice through which blood will flow when implanted from an inflow side to an outflow side of the implant, the implant including a pliant sealing edge extending outward therefrom having a plurality of generally axial slits that open radially outward, the system further including a plurality of knotless suture fasteners attached to and distributed around the sealing edge, each fastener having an axial slot sized to receive a suture and facing radially outward so as to align with one of the axial slits;
pre-installing a plurality of anchoring sutures at the annulus, each anchoring suture being passed through the annulus with at least one free end extending away from the annulus;
passing each of the free ends of the anchoring sutures radially inward through one of the axial slits in the sealing edge and into the aligned suture fastener slot;
advancing the cardiac implant distally until the sealing edge seats against the annulus; and
deploying the suture fasteners to clamp onto the free ends of the anchoring sutures.

2. The method of claim 1, wherein the cardiac implant is a prosthetic heart valve, comprising:
occluding members that provide one-way flow through the valve, and
wherein the pliant sealing edge comprises a sealing ring secured to the outside of the valve.

3. The method of claim 1, wherein the implant is an annuloplasty ring, wherein an inner frame comprises a metallic core and the pliant sealing edge surrounds the core and has a fabric cover.

4. The method of claim 1, wherein the cardiac implant is a valved conduit comprising a valve having a conduit coupled thereto and the pliant sealing edge surrounds an inflow end thereof.

5. The method of claim 1, wherein each fastener has an open state which permits a suture to slide axially therethrough and a closed state which prevents distal axial movement of the suture through the suture fasteners, wherein the step of deploying occurs prior to the step of advancing.

6. The method of claim 1, wherein the plurality of suture fasteners are at least partially embedded into the sealing edge and secured therein.

7. The method of claim 6, wherein each suture fastener has a proximal end flange extending outward therefrom sufficiently large to prevent the fastener from pulling through the sealing ring in a distal direction.

8. The method of claim 1, wherein each suture fastener includes a retention member coupled thereto in an open state which permits a suture to slide axially therethrough and when removed converts the fastener to a closed state which prevents axial movement of the suture in at least one direction.

9. The method of claim 8, wherein each suture fastener has an outer wall defining a lumen extending from a proximal end to a distal end and a collapsible wall structure, wherein the collapsible wall structure is held outward by the retention member in the open state and the collapsible wall structure in a closed state restricts movement of a suture through the fastener in at least one direction, the method including removal of the retention members such that the collapsible wall structure collapses inward to convert the fastener to the closed state.

10. The method of claim 8, wherein a plurality of the retention members are tethered together, the method including sequentially removing the retention members from adjacent fasteners.

11. A method of securing a prosthetic heart valve to a heart valve annulus, comprises:
providing a pre-assembled prosthetic heart valve system including a prosthetic heart valve defining a flow orifice through which blood will flow when implanted from an inflow side to an outflow side thereof and occluding members that provide one-way flow through the valve, the valve including a pliant sealing ring extending outward therefrom having a plurality of generally axial slits that open radially outward, the system further including a plurality of knotless suture fasteners attached to and distributed around the sealing edge, each fastener having an axial slot sized to receive a suture and facing radially outward so as to align with one of the axial slits;
pre-installing a plurality of anchoring sutures at the annulus, each anchoring suture being passed through the annulus with at least one free end extending away from the annulus;
passing each of the free ends of the anchoring sutures radially inward through one of the axial slits in the sealing ring and into the aligned suture fastener slot;
advancing the valve distally until the sealing ring seats against the annulus; and
deploying the suture fasteners to clamp onto the free ends of the anchoring sutures.

12. The method of claim 11, wherein each fastener has an open state which permits a suture to slide axially therethrough and a closed state which prevents distal axial movement of the suture through the suture fasteners, wherein the step of deploying occurs prior to the step of advancing.

13. The method of claim 11, wherein the plurality of suture fasteners are at least partially embedded into the sealing ring and secured therein.

14. The method of claim 13, wherein each suture fastener has a proximal end flange extending outward therefrom sufficiently large to prevent the fastener from pulling through the sealing ring in a distal direction.

15. The method of claim 11, wherein each suture fastener includes a retention member coupled thereto in an open state which permits a suture to slide axially therethrough and when removed converts the fastener to a closed state which prevents axial movement of the suture in at least one direction.

16. The method of claim 15, wherein each suture fastener has an outer wall defining a lumen extending from a proximal end to a distal end and a collapsible wall structure, wherein the collapsible wall structure is held outward by the retention member in the open state and the collapsible wall structure in a closed state restricts movement of a suture through the fastener in at least one direction, the method including removal of the retention members such that the collapsible wall structure collapses inward to convert the fastener to the closed state.

17. The method of claim 15, wherein a plurality of the retention members are tethered together, the method including sequentially removing the retention members from adjacent fasteners.

18. The method of claim 11, wherein there are only three of the suture fasteners evenly spaced around the sealing ring, and the valve has an inner frame that partly extends in an outflow direction to form three cantilevered commissures evenly distributed around the flow axis that support flexible leaflets defining the occluding members, and the valve further includes a plastically-expandable anchoring skirt extending from an inflow end thereof, the three suture fasteners being located around the sealing ring intermediate the commissures, the method including first deploying the three suture fasteners and then outwardly expanding the plastically-expandable anchoring skirt.

19. The method of claim 11, further including severing each of the free ends of the anchoring sutures close to a proximal end of the respective suture fastener.

20. The method of claim 11, wherein each suture fastener comprises:
- a bifurcated locking clamp including a pair of substantially similar clamp halves each having an exterior surface and an inner surface facing the inner surface of the other clamp half to form the slot therebetween, the clamp halves being connected for movement toward or away from one another while being fixed axially with respect to one another, wherein a suture extends through the slot between the inner surfaces of the clamp halves;
- a biasing member positioned on the outside of the locking clamp having a relaxed size that, in the absence of an object in the slot, urges the inner surfaces of the clamp halves together; and
- a retention member positioned between the clamp halves against the force of the biasing member and having a thickness that maintains the slot width large enough to permit passage of a suture therethrough, the method including removal of the retention member to permit the biasing member to urge the inner surfaces of the clamp halves together and clamp the suture therebetween.

* * * * *